United States Patent [19]

Erhardt et al.

[11] Patent Number: 4,906,661

[45] Date of Patent: Mar. 6, 1990

[54] ESTERS OF ARYLOXYPROPANOLAMINE DERIVATIVES

[75] Inventors: Paul W. Erhardt, Long Valley, N.J.; William L. Matier, Libertyville, Ill.

[73] Assignee: E. I. Du Pont de Nemours and Company, Wilmington, Del.

[21] Appl. No.: 308,575

[22] Filed: Feb. 10, 1989

Related U.S. Application Data

[60] Division of Ser. No. 93,669, Sep. 8, 1987, Pat. No. 4,804,677, which is a division of Ser. No. 923,993, Oct. 28, 1986, Pat. No. 4,692,446, which is a division of Ser. No. 691,787, Jan. 16, 1985, Pat. No. 4,623,652, which is a continuation-in-part of Ser. No. 580,295, Feb. 21, 1984, abandoned, which is a continuation of Ser. No. 320,772, Nov. 12, 1981, abandoned.

[51] Int. Cl.$^4$ .................. A61K 31/255; A61K 31/24; C07C 155/02

[52] U.S. Cl. ...................... 514/517; 514/522; 514/524; 514/538; 514/539; 558/48; 558/49; 558/412; 558/413; 560/13

[58] Field of Search ............... 514/517, 522, 524, 600, 514/602, 605, 538, 539; 558/48, 49, 412, 413; 564/79, 84, 86, 87, 88; 560/13

[56] References Cited

U.S. PATENT DOCUMENTS 4,025,646  5/1977  Köppe et al. .................. 514/424
4,083,992  4/1978  Smith .................. 564/86

Primary Examiner—Joseph Paul Brust
Assistant Examiner—Mary Sue Howard
Attorney, Agent, or Firm—Gildo E. Fato

[57] ABSTRACT

Novel compounds of the general formula

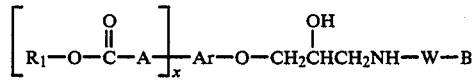

wherein $R_1$ is lower alkyl, lower cycloalkyl, lower alkenyl, lower alkynyl, lower alkyl carboxymethyl, aryl carboxymethyl, aryl, or aralkyl; A is a direct bond, lower alkylene, or lower alkenylene; x is 1 or 2, provided that when x is greater than 1, different occurrences of the

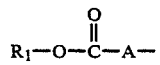

group may be the same or different; Ar is heterocyclic, unsubstituted aromatic or aromatic substituted with lower alkyl, lower alkenyl, lower alkynyl, lower alkoxy, halogen, acetamido, amino, nitro, lower alkylamino, hydroxy, lower hydroxyalkyl or cyano; W is alkylene containing from 1 to about 10 carbon atoms; and B is $-NR_2COR_3$, $-NR_2CONR_3R_4$, $-NR_2SO_2R_3$, $-NR_2SO_2NR_3R_4$, or $-NR_2COOR_5$, wherein $R_2$, $R_3$, $R_4$ and $R_5$ may be the same or different and may be hydrogen, alkyl, alkoxyalkyl, alkoxyaryl, cycloalkyl, alkenyl, alkynyl, aryl, heteroaryl, or aralkyl, except that $R_3$ and $R_5$ are not hydrogen when B is $-NR_2SO_2R_3$ or $-NR_2COOR_5$, or $R_3$ and $R_4$ may together with N form a 5 to 7 membered heterocyclic group; and the pharmaceutically acceptable salts thereof.

20 Claims, No Drawings

ESTERS OF ARYLOXYPROPANOLAMINE DERIVATIVES

This application is a divisional of 07/93,669 filed 09/08/87, now U.S. Pat. No. 4,804,677 which is a division of 06/923,993 filed 10/28/86, now U.S. Pat. No. 4,692,446, which is a division of 06/691,787 filed 01/16/85 now U.S. Pat. No. 4,623,652 which is a continuation-in-part of 06/580,295 filed 02/21/84 now abandoned which is a continuation of 06/320,772 filed 11/12/81, now abandoned.

BACKGROUND OF THE INVENTION

Compounds of the present invention are useful because of their valuable pharmaceutical properties. They exhibit $\beta$-adrenergic blocking activity and are also useful in the treatment of glaucoma.

The present invention also relates to the treatment or prophylaxis of cardiac disorders. More particularly, the invention relates to a novel method of treatment or prophylaxis of cardiac disorders which comprises administration of $\beta$-adrenergic blocking agents and to compounds useful in such method.

The therapeutic and prophylactic uses of compounds which block sympathetic nervous stimulation of $\beta$-adrenergic receptors in the heart, lungs, vascular system and other organs are well documented. Typically, such compounds are administered therapeutically to patients suffering from ischemic heart disease or myocardial infarction for the purpose of reducing heart work, i.e., heart rate and contractile force. Reducing heart work reduces oxygen demand, and may also actually increase oxygen supply. Thus reducing heart work can aid in the prevention of further tissue damage and can relieve angina pectoris.

$\beta$-Adrenergic stimulation may also aggravate or cause arrhythmias because of increased levels of catecholamines. Thus $\beta$-blocking agents may be employed to reduce the risks of arrhythmias.

Some of the compounds of the present invention selectively block $\beta$-adrenergic receptors in various organs. Beta receptors in the heart are generally referred to as $\beta_1$ receptors, and those associated with vasodilation and bronchodilation are $\beta_2$ receptors. Selective $\beta$-blockers are preferred for the treatment of cardiac disorders, because they may have less potential to cause hypertension or bronchoconstriction. A number of $\beta_1$ selective adrenergic blocking agents have been discovered [Smith, L. H., *J. Appl. Chem. Biotechnol.*, 28, 201-202 (1978)]. Most such compounds are structural variations of 1-amino-3-aryloxy-2-propanol.

Heretofore, the emphasis in $\beta$-blocker research has been to develop compounds which can be administered to cardiac patients over long periods of time. However, often it is desirable in the critical care setting to quickly reduce heart work or improve rhythmicity during a cardiac crisis, e.g., during or shortly after a myocardial infarction. Conventional $\beta$-blocking agents can be employed for such treatment, but their duration of action may be much longer than desired by the physician. A $\beta$-blocking agent possessing a long duration of action does not allow precise control of heart work or prompt reversal of the $\beta$-blocking effect, which may be required in a critical care setting. For instance, if heart output becomes dangerously low, it is desirable to quickly reduce or eliminate $\beta$-blocking activity. The lingering activity of available $\beta$-blocking agents can be counter-productive and can greatly complicate the therapeutic decisions required of the physician during such critical care of cardiac patients.

Accordingly, there is a need for a pharmaceutical preparation and method of treatment, employing a $\beta$-adrenergic blocking agent having a short duration of action.

Compounds of the present invention are also useful for the treatment of glaucoma or lowering of intraocular pressure by topical administration of the compounds to the eye. Compounds with short duration in the systemic circulation, but with good stability in ocular fluid, are particularly useful since they have a low potential for producing systemic side effects.

Glaucoma is a condition of the eye characterized by increased intraocular pressure. Untreated, the condition can eventually lead to irreversible retinal damage and blindness. Conventional therapy for glaucoma has involved topical administration of pilocarpine and/or epinephrine, administered to the eye several time daily.

The use of various $\beta$-blocking agents to lower intraocular pressure is well documented. For example, U.S. Pat. No. 4,195,085 to Stone discloses a method for treatment of glaucoma by the optical administration of a $\beta$-blocking compound, timolol maleate. U.S. Pat. No. 4,127,674 discloses a method of treating glaucoma with labetalol, a known antagonist of both alpha and beta adrenergic receptors. However, these methods also possess significant drawbacks, in that the absorption of the $\beta$-blocking compound into the systemic circulation can cause undesirable side effects. Such side effects result from prolonged $\beta$-blocking action on the heart, bronchioles and blood vessels. For example, according to *Physicians' Desk Reference*, Charles E. Baker, Jr., 35th Edition, 1981, p. 1233, adverse reactions to the topical use of timolol maleate can include bronchospasm and heart failure, as well as cardiac conduction defects. Accordingly, there is a need for a method of treatment for glaucoma or for lowering intraocular pressure which is relatively free of unwanted systemic side-effects.

SUMMARY OF THE INVENTION

The present invention relates to compounds of the formula

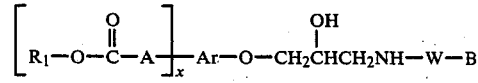

wherein $R_1$ is lower alkyl, lower cycloalkyl, lower alkenyl, lower alkynyl, lower alkyl carboxymethyl, aryl carboxymethyl, aryl, or aralkyl; A is a direct bond, lower alkylene, or lower alkenylene; x is 1 or 2, provided that when x is greater than 1, different occurrences of the

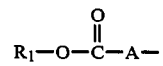

group may be the same or different; Ar is heterocyclic, unsubstituted aromatic or aromatic substituted with lower alkyl, lower alkenyl, lower alkynyl, lower alkoxy, halogen, acetamido, amino, nitro, lower alkylamino, hydroxy, lower hydroxyalkyl or cyano; W is alkylene containing from 1 to about 10 carbon atoms;

and B is —NR$_2$COR$_3$, —NR$_2$CONR$_3$R$_4$, —NR$_2$SO$_2$R$_3$, —NR$_2$SO$_2$NR$_3$R$_4$, or —NR$_2$COOR$_5$, wherein R$_2$, R$_3$, R$_4$ and R$_5$ and may each be hydrogen, alkyl, alkoxyalkyl, alkoxyaryl, cycloalkyl, alkenyl, alkynyl, aryl, heteroaryl, or aralkyl, except that R$_3$ and R$_5$ are not hydrogen when B is —NR$_2$SO$_2$R$_3$ or —NR$_2$COOR$_5$, or R$_3$ and R$_4$ may together with N form a 5 to 7 membered heterocyclic group; and the pharmaceutically acceptable salts thereof.

DETAILED DESCRIPTION OF THE INVENTION

The present invention relates to compounds of the formula

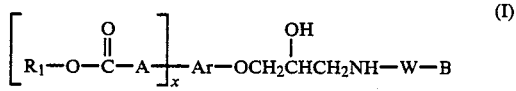 (I)

wherein R$_1$ represents lower alkyl of straight or branched carbon chains from 1 to about 10 carbon atoms, lower cycloalkyl of from 3 to about 7 carbon atoms, lower alkenyl of from 2 to about 5 carbon atoms, lower alkynyl of from 3 to about 5 carbon atoms, lower alkyl carboxymethyl in which the alkyl portion contains from 1 to about 5 carbon atoms, aryl carboxymethyl in which the aryl portion contains from 6 to about 10 carbon atoms, aryl of from 6 to about 10 carbon atoms or aralkyl wherein the alkyl portion contains from 1 to about 6 carbon atoms and the aryl portion represents substituted or unsubstituted monocyclic or polycyclic aromatic or heterocyclic ring systems of from 6 to about 10 carbon atoms; A represents a direct bond between the ester group and Ar, lower alkylene of from 1 to about 10 carbon atoms, or alkenylene of from 2 to about 10 carbon atoms; x represents 1 or 2, provided that when x is greater than 1, different occurrences of the

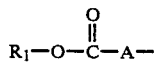

group may be the same or different; Ar represents a substituted or unsubstituted aromatic group, including monocyclic, polycyclic and heterocyclic ring systems, wherein aromatic substituents include lower alkyl of from 1 to about 10 carbon atoms, lower alkenyl of from 2 to about 10 carbon atoms, lower alkynyl of from 2 to about 10 carbon atoms, lower alkoxy of from 1 to about 10 carbon atoms, halogen, acetamido, amino, nitro, lower alkylamino of from 1 to about 10 carbon atoms, hydroxy, lower hydroxyalkyl of from 1 to about 10 carbon atoms, and cyano; W represents a straight or branched chain alkylene containing from 1 to about 10 carbon atoms; and B represents —NR$_2$COR$_3$, —NR$_2$CONR$_3$R$_4$, —NR$_2$SO$_2$R$_3$, —NR$_2$SO$_2$NR$_3$R$_4$, or —NR$_2$COOR$_5$ wherein R$_2$, R$_3$, R$_4$ and R$_5$ may be the same or different and may be hydrogen, alkyl of from 1 to about 10 carbon atoms, alkoxyalkyl wherein the alkyl groups may be the same or different and contain from 1 to about 10 carbon atoms, cycloalkyl of from 3 to about 8 carbon atoms, alkenyl of from 3 to about 10 carbon atoms, alkynyl of from 3 to about 10 carbon atoms, aryl which includes substituted or unsubstituted monocyclic or polycyclic aromatic or heterocyclic ring systems of from 2 to about 10 carbon atoms such as phenyl, thiophenyl, imidazole, oxazole, indole, and the like; or aralkyl wherein the alkyl portion contains from 1 to about 6 carbon atoms and the aryl portion represents substituted or unsubstituted monocyclic or polycyclic aromatic or heterocyclic ring systems of from 2 to about 10 carbon atoms such as benzyl, phenethyl, 3,4-dimethoxyphenethyl, 1,1-dimethyl-2-(3-indolyl)ethyl and the like; except that R$_3$ and R$_5$ are not hydrogen when B is —NR$_2$SO$_2$R$_3$ or —NR$_2$COOR$_5$, or R$_3$ and R$_4$ may together with N form a 5 to 7 membered heterocyclic group such as pyrrolidine, piperidine, piperazine, morpholine, or thiomorpholine. Such compounds may be administered as their pharmaceutically acceptable acid addition salts, e.g., as the hydrochloride, sulfate, phosphate, gluconate, tartrate, etc.

The ester substituent, R$_1$, in preferred compounds, is lower alkyl of from 1 to about 5 carbon atoms, such as methyl, ethyl, n-butyl, n-pentyl, and the like; lower alkenyl of from 2 to about 5 carbon atoms, such as ethenyl, 2-propenyl, 2-methyl-3-butenyl and the like, lower alkynyl of from 3 to about 5 carbon atoms, such as propargyl, methylpropargyl and the like, or lower cycloalkyl of from 3 to about 5 carbon atoms such as cyclopropyl, cyclopentyl, 2-methylcyclopropyl, and the like.

Preferred aromatic substituents include lower alkyl of from 1 to about 5 carbon atoms, lower alkenyl of from 2 to about 5 carbon atoms, lower alkoxy of from 1 to about 5 carbon atoms, halogen, acetamido, amino, nitro, lower alkylamino of from 1 to about 5 carbon atoms, hydroxy, lower hydroxyalkyl of from 1 to about 5 carbon atoms, and cyano. Particularly preferred aromatic substituents are lower alkyl of from 1 to about 5 carbon atoms, fluoro, chloro, cyano, and alkoxy.

In particularly preferred compounds, the ester substituent R$_1$ is methyl or ethyl; A is a direct bond, lower alkylene of from 1 to about 5 carbon atoms, such as methylene, ethylene, butylene and the like, or lower alkenylene of from 2 to about 5 carbon atoms, such as ethenylene, 2-propenylene, 2-butenylene, and the like; x is 1 or 2; Ar is phenyl or thiadiazolyl; W is alkylene of from 2 to about 4 carbon atoms, such as ethylene, methylethylene, or dimethylethylene; and R$_2$ is hydrogen.

Included in the present invention are compounds of the formula

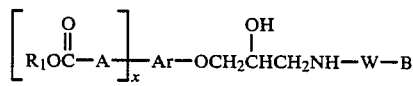

wherein R$_1$ is lower alkyl, lower cycloalkyl, lower alkenyl, lower alkynyl, lower alkyl carboxymethyl, aryl carboxymethyl, aryl, or aralkyl; A is a direct bond, lower alkylene, or lower alkenylene; x is 1 or 2, provided that when x is greater than 1, different occurrences of the

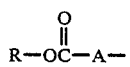

group may be the same or different; Ar is heterocyclic, unsubstituted aromatic or aromatic substituted with lower alkyl, lower alkenyl, lower alkynyl, lower alkoxy, halogen, acetamido, amino, nitro, lower alkylamino, hydroxy, lower hydroxyalkyl, or cyano; W is alkylene containing from 1 to about 10 carbon atoms; B is —NR$_2$COR$_3$, —NR$_2$CONR$_3$, —NR$_2$SO$_2$R$_3$, —NR- $-2SO_2NR_3R_4$ or $-NR_2COOR_5$ wherein $R_2$, $R_3$, $R_4$, and $R_5$ may be the same or different and may be hydrogen, alkyl of from 1 to about 6 carbon atoms, alkoxy wherein the alkyl group contains from 1 to about 6 carbon atoms, alkoxyalkyl wherein the alkyl groups may be the same or different and each contain from 1 to about 6 carbon atoms, cycloalkyl of from 3 to about 8 carbon atoms, alkenyl of from 2 to about 6 carbon atoms, alkynyl of from 2 to about 6 carbon atoms, aralkyl wherein the alkyl group contains from 1 to about 6 carbon atoms, or a substituted or unsubstituted aromatic or heterocyclic group, except that $R_3$ and $R_5$ are not hydrogen when B is $-NR_2SO_2R_3$ or $-NR_2COOR_5$, or $R_3$ and $R_4$ may together with N form a 5 to 7 membered heterocyclic group; and the pharmaceutically acceptable salts thereof.

The present invention also relates to compounds of the formula

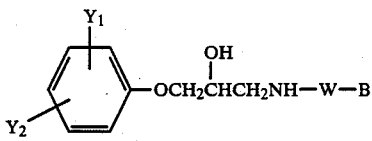

wherein $Y_1$ and $Y_2$ are each selected from the group consisting of hydrogen and $ACOOR_1$ wherein $R_1$ is alkyl of from 1 to about 6 carbon atoms, provided that at least one is $ACOOR_1$; A is a direct bond, alkylene of from 1 to about 5 carbon atoms or alkenylene of about 2 to about 5 carbon atoms; W is alkylene of from 1 to about 6 carbon atoms; and B is $-NR_2COR_3$, $-NR_2CONR_3R_4$, $-NR_2SO_2R_3$, $-NR_2SO_2NR_3R_4$, or $-NR_2COOR_5$ wherein $R_2$ is hydrogen and $R_3$, $R_4$ and $R_5$ may be the same or different and may be hydrogen, alkyl of from 1 to about 6 carbon atoms, alkoxy wherein the alkyl group contains from 1 to about 6 carbon atoms, cycloalkyl of from 3 to about 8 carbon atoms, alkoxyalkyl wherein the alkyl groups may be the same or different and each contain from 1 to about 5 carbon atoms, phenyl, phenyl substituted with alkyl of from 1 to about 4 carbon atoms, alkoxy of from 1 to about 4 carbon atoms, halogen, amino, nitro, hydroxy, hydroxyalkyl wherein the alkyl group contains from 1 to about 4 carbon atoms, alkamino wherein the alkyl group contains from 1 to about 4 carbon atoms, phenylalkyl wherein the alkyl group contains from 1 to about 4 carbon atoms and the phenyl group is unsubstituted or substituted with alkyl of from 1 to about 4 carbon atoms, alkoxy of from 1 to about 4 carbon atoms, halogen, amino, nitro, hydroxy, hydroxyalkyl wherein the alkyl group contains from 1 to about 4 carbon atoms, alkamino wherein the alkyl group contains from 1 to about 4 carbon atoms, cyano, or a 5 to 7 membered heterocyclic group, except that $R_3$ and $R_5$ are not hydrogen when B is $-NR_2SO_2R_3$ or $-NR_2COOR_5$, or $R_3$ and $R_4$ may together with N form a 5 to 7 membered heterocyclic group; and the pharmaceutically acceptable salts thereof.

Included in the present invention are compounds of the formula

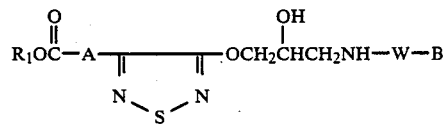

wherein $R_1$ is alkyl of from 1 to about 6 carbon atoms; A is a direct bond, alkylene of from 1 to about 5 carbon atoms or alkenylene of from 2 to about 5 carbon atoms; W is alkylene of from 1 to about 6 carbon atoms; and B is $-NR_2COR_3$, $-NR_2CONR_3R_4$, $-NR_2SO_2R_3$, $-NR_2SO_2NR_3R_4$, or $-NR_2COOR_5$ wherein $R_2$ is hydrogen and $R_3$, $R_4$ and $R_5$ may be the same or different and may be hydrogen, alkyl of from 1 to about 6 carbon atoms; alkoxy wherein the alkyl group contains from 1 to about 6 carbon atoms, cycloalkyl of from 3 to about 8 carbon atoms, alkoxyalkyl wherein the alkyl groups may be the same or different and each contain from 1 to about 5 carbon atoms, phenyl, pheryl substituted with alkyl of 1 from to about 4 carbon atoms, alkoxy of from 1 to about 4 carbon atoms, halogen, amino, nitro, hydroxy, hydroxyalkyl wherein the alkyl group contains from 1 to about 4 carbon atoms, alkamino wherein the alkyl group contains from 1 to about 4 carbon atoms, phenylalkyl wherein the alkyl group contains from 1 to about 4 carbon atoms and the phenyl group is unsubstituted or substituted with alkyl of from 1 to about 4 carbon atoms, alkoxy of from 1 to about 4 carbon atoms, halogen, amino, nitro, hydroxy, hydroxyalkyl wherein the alkyl group contains from 1 to about 4 carbon atoms, alkamino wherein the alkyl group contains from 1 to about 4 carbon atoms, cyano, or a 5 to 7 membered heterocyclic group, except that $R_3$ and $R_5$ are not hydrogen when B is $-NR_2SO_2R_3$ or $-NR_2COOR_5$, or $R_3$ and $R_4$ may together with N form a 5 to 7 membered heterocyclic group; and the pharmaceutically acceptable salts thereof.

Also included in the present invention are compounds of the following formulae:

(a) Compounds of the formula

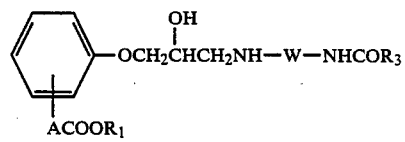

wherein $R_1$ is alkyl of from 1 to about 4 carbon atoms; A is a direct bond, alkylene of from 1 to about 3 carbon atoms, or alkenylene of from 2 to about 5 carbon atoms; W is alkylene of from 1 to about 6 carbon atoms; and $R_3$ is alkyl of from 1 to about 6 carbon atoms, alkoxy wherein the alkyl group contains from 1 to about 5 carbon atoms, phenyl which may be unsubstituted or substituted with alkyl of from 1 to about 4 carbon atoms or alkoxy of from 1 to about 4 carbon atoms, phenylalkyl wherein the alkyl group contains from 1 to about 4 carbon atoms and the phenyl group may be unsubstituted or substituted with alkyl of from 1 to about 4 carbon atoms or alkoxy of 1 to 4 carbon atoms, cycloalkyl of 3 to 7 carbon atoms, or a 5 to 7 membered heterocyclic group; and the pharmaceutically acceptable salts thereof.

(b) Compounds of the formula

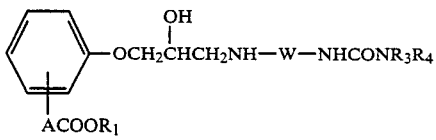

wherein $R_1$ is alkyl of from 1 to about 4 carbon atoms; A is a direct bond, alkylene of from 1 to about 3 carbon atoms, or alkenylene of from 2 to about 5 carbon atoms; W is alkylene of from 1 to about 6 carbon atoms; and $R_3$ and $R_4$ may be the same or different and represent hydrogen, alkyl of from 1 to about 4 carbon atoms, phenyl which may be unsubstituted or substituted with alkyl of from 1 to about 4 carbon atoms or alkoxy of from 1 to about 4 carbon atoms, phenylalkyl wherein the alkyl group contains from 1 to about 4 carbon atoms and the phenyl group may be unsubstituted or substituted with alkyl of from 1 to about 4 carbon atoms or alkoxy of from 1 to about 4 carbon atoms, cycloalkyl of from 3 to about 7 carbon atoms, or $R_3$ and $R_4$ may together with N form a 5 to 7 membered heterocyclic group; and the pharmaceutically acceptable salts thereof.

(c) Compounds of the formula

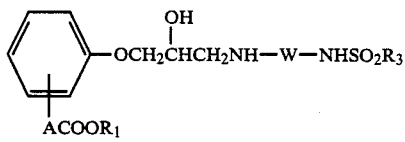

wherein $R_1$ is alkyl of from 1 to about 4 carbon atoms; A is a direct bond, alkylene of from 1 to about 3 carbon atoms, or alkenylene of from 2 to about 5 carbon atoms; W is alkylene of from 1 to about 6 carbon atoms; and $R_3$ is alkyl of from 1 to about 6 carbon atoms, alkoxy wherein the alkyl group contains from 1 to about 5 carbon atoms, phenyl which may be unsubstituted or substituted with alkyl of from 1 to about 4 carbon atoms or alkoxy of from 1 to about 4 carbon atoms, phenylalkyl wherein the alkyl group contains from 1 to about 4 carbon atoms and the phenyl group may be unsubstituted or substituted with alkyl of from 1 to about 4 carbon atoms or alkoxy of from 1 to about 4 carbon atoms, cycloalkyl of from 3 to about 7 carbon atoms, or a 5 to 7 membered heterocyclic group; and the pharmaceutically acceptable salts thereof.

(d) Compounds of the formula

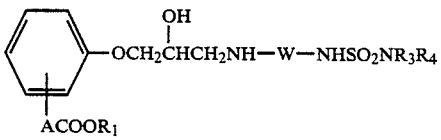

wherein $R_1$ is alkyl of from 1 to about 4 carbon atoms; A is a direct bond, alkylene of from 1 to about 3 carbon atoms, or alkenylene of from 2 to about 5 carbon atoms; W is alkylene of from 1 to about 6 carbon atoms; and $R_3$ and $R_4$ may be the same or different and represent hydrogen, alkyl of from 1 to about 4 carbon atoms, phenyl which may be unsubstituted or substituted with alkyl of from 1 to about 4 carbon atoms or alkoxy of from 1 to about 4 carbon atoms, phenylalkyl wherein the alkyl group contains from 1 to about 4 carbon atoms and the phenyl group may be unsubstituted or substituted with alkyl of from 1 to about 4 carbon atoms or alkoxy of from 1 to about 4 carbon atoms, cycloalkyl of from 3 to about 7 carbon atoms, or $R_3$ and $R_4$ may together with N form a 5 to 7 membered heterocyclic group; and the pharmaceutically acceptable salts thereof.

(e) Compounds of the formula

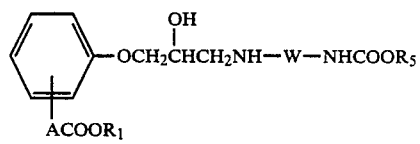

wherein $R_1$ is alkyl of from 1 to about 4 carbon atoms, A is a direct bond, alkylene of from 1 to about 3 carbon atoms, or alkenylene of from 2 to about 5 carbon atoms; W is alkylene of from 1 to about 6 carbon atoms; and $R_5$ is alkyl of from 1 to about 5 carbon atoms; alkoxyalkyl wherein the alkyl groups may be the same or different and contain from 1 to about 5 carbon atoms; phenyl which may be unsubstituted or substituted with alkyl of from 1 to about 4 carbon atoms or alkoxy of from 1 to about 4 carbon atoms, phenylalkyl wherein the alkyl group contains from 1 to about 4 carbon atoms and the phenyl group may be unsubstituted or substituted with alkyl of from 1 to about 4 carbon atoms or alkoxy of from 1 to about 4 carbon atoms, or cycloalkyl of from 3 to about 7 carbon atoms; and the pharmaceutically acceptable salts thereof.

Compounds of the present invention exist as two stereoisomers due to the presence of an asymmetric carbon atom. This invention includes either stereoisomeric form, as well as racemic mixtures. For compounds in which A, $R_2$, $R_3$, $R_4$, or $R_5$ represent alkenyl or alkenylene, both cis and trans isomers are within the scope of the invention. Where Ar is a substituted aromatic ring, substituents claimed may be in the ortho, meta or para positions to the propoxy side-chain.

The compounds described herein may be prepared by any suitable procedure. Compounds prepared as the acid addition salts may be converted to the free base by reaction with an appropriate base such as sodium carbonate or sodium bicarbonate. The compounds are advantageously prepared by reacting an appropriate phenol derivative with epichlorohydrin in the presence of a base to form a 1,2-epoxy-3-aryloxypropane derivative according to the following reaction:

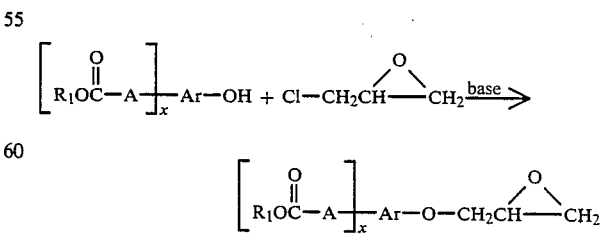

wherein $R_1$, A, x and Ar are defined as hereinbefore. The 1,2-epoxy-3-aryloxy-propane so prepared may then be reacted with an amine to form the desired product:

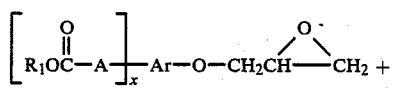

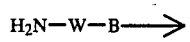

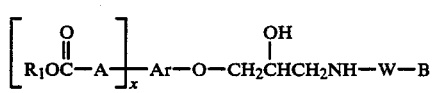

wherein $R_1$, $A$, $x$, $Ar$, $W$ and $B$ are defined as hereinbefore. This reaction is preferably conducted in an alcoholic solvent identical to the ester adduct to prevent alcoholysis side reactions, e.g., when $R_1$ is methyl, the reaction solvent is preferably methanol.

Alternatively, the compounds of the present invention, particularly the compounds of Formula I wherein B is $-NR_2SO_2NR_3R_4$, may be prepared by reacting the 1,2-epoxy-3-aryloxy-propane with an N-benzyl-protected amine. The protecting group is then conveniently removed by hydrogenolysis over a palladium catalyst to provide the desired compound as shown below:

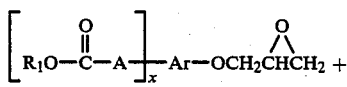

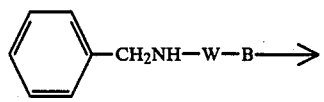

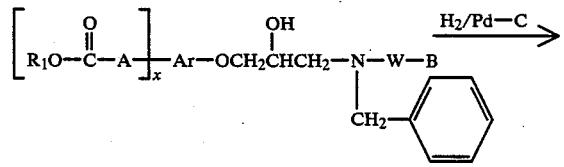

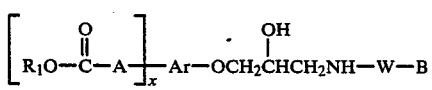

wherein $R_1$, $Ar$, $x$, $Ar$, $W$, and $B$ are defined as hereinbefore.

The phenol derivatives used as starting materials in the reaction scheme described above are generally commercially available compounds or may be prepared by methods known in the art.

The amines, $H_2N$-$W$-$B$, wherein $W$ and $B$ are defined as hereinbefore may be prepared by the following methods:

(a) For amidoalkylamines ($B=NR_2COR_3$)

$$H_2N\text{-}W\text{-}NHR_2 + R_3COOC_2H_5 \rightarrow H_2NW\text{-}NHCOR_3$$

wherein $W$, $R_2$ and $R_3$ are as defined as hereinbefore.

(b) For alkoxycarbonylaminoalkylamines ($B=NR_2COOR_5$), either of two methods may be used:

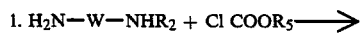

2. 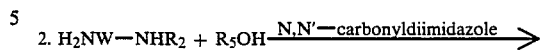

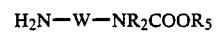

wherein $W$, $R_2$ and $R_5$ are defined as hereinbefore.

(c) For ureidoalkylamines ($B=NR_2CONR_3R_4$) any of four methods may be used:

(1) 

(2) 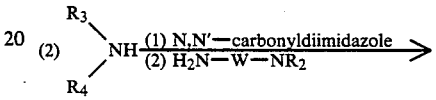

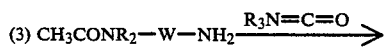

(3) $CH_3CONR_2$-$W$-$NH_2 \xrightarrow{R_3N=C=O}$

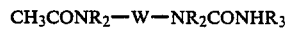

 HCl

(4) 

wherein $W$, $R_2$, $R_3$ and $R_4$ are defined as hereinbefore.

(d) For sulfonamidoalkylamines ($B=NR_2SO_2R_3$):

$$H_2N\text{-}W\text{-}NHR_2 + R_3SO_2Cl \rightarrow H_2N\text{-}W\text{-}NR_2SO_2R_3$$

wherein $W$, $R_2$ and $R_3$ are defined as hereinbefore.

(e) For sulfamidoalkylamines ($B=NR_2SO_2NR_3R_4$)

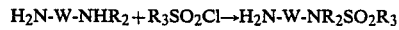

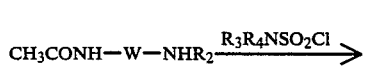

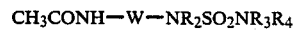

 HCl

wherein $W$, $R_2$, $R_3$ and $R_4$ are defined as hereinbefore.

(f) Protected N-benzylamine intermediates,

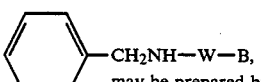

may be prepared by the following method:

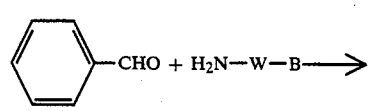

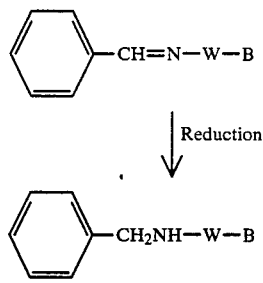

wherein W and B are defined as hereinbefore. The reduction may be accomplished by hydrogenation over a catalyst such as palladium-on-carbon or by hydride reagents such as sodium cyanoborohydride.

The syntheses of some of the starting materials for compounds of the present invention are described in copending U.S. patent application Ser. No. 211,345 which is hereby incorporated by reference.

When used for the treatment of cardiac disorders, the compounds of this invention are advantageously administered parenterally, e.g., by intravenous injection or intravenous infusion. Certain compounds having a longer duration of action may be administered orally. Formulations for intravenous injection preferably include the active compound as a soluble acid addition salt in a properly buffered isotonic solution.

The dosage administered to a patient and the duration of infusion will depend upon the patient's needs and the particular compounds employed. For short periods of infusion, e.g., less than about three hours, the duration of effect is thought to be determined by both metabolic effects and distribution phenomena. For relatively long periods of infusion, e.g., greater than about three hours, the duration of effect is thought to depend largely on metabolic effects. Accordingly, although the present methods and compounds are generally useful for short term infusion therapy, certain compounds are preferred for longer durations of infusion. The compounds have been found to be generally non-toxic within conventional dosage ranges. Dosages of about 0.001 to about 100 mg. per kg. of body weight per hour are generally employed with preferred dosages ranging from about 0.01 to about 10 mg. per kg. of body weight per hour.

When used for the treatment of glaucoma, the compounds of this invention are advantageously administered topically to the eye in the form of a solution, ointment, or solid insert such as is described in U.S. Pat. No. 4,195,085. Formulations may contain the active compound, preferably in the form of a soluble acid addition salt, in amounts ranging from about 0.01 to about 10% by wt., preferably from about 0.5% to about 5% by wt. Unit dosages of the active compound can range from about 0.001 to about 5.0 mg., preferably from about 0.05 to about 2.0 mg. The dosage administered to a patient will depend upon the patient's needs and the particular compounds employed.

Carriers used in the preparations of the present invention are preferably non-toxic pharmaceutical organic or inorganic compositions such as water; mixtures of water and water-miscible solvents, such as lower alcohols; mineral oils; petroleum jellies; ethyl cellulose; polyvinylpyrrolidone and other conventional carriers. In addition, the pharmaceutical preparations may also contain additional components such as emulsifying, preserving, wetting and sterilizing agents. These include polyethylene glycols 200, 300, 400 and 600, carbowaxes 1,000; 1,500; 4,000; 6,000 and 10,000, bacteriocidal components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The method of treatment of this invention advantageously involves the topical administration of eye drops containing the active compound. Formulations for eye drops preferably include the active compound as a soluble acid addition salt in a properly buffered, sterile, aqueous isotonic solution.

The compounds of the present invention are ester group-containing β-blockers that have a selective, localized, β-blocking effect in the eye after topical administration. Such compounds are thought to be rapidly metabolized by plasma and/or liver esterases into inactive by-products, upon entering the systemic circulation. It has been discovered that these same compounds are relatively stable in ocular fluids, i.e., lacrimal fluids and aqueous humor. Consequently, such compounds are useful for the treatment of glaucoma or for lowering intraocular pressure since they remain stable when topically applied to the eye but rapidly metabolize when subsequently absorbed into the systemic circulation.

Some of the compounds break down in the aqueous humor more rapidly than others. Such compounds may advantageously be employed when only a temporary reduction in intraocular pressure is desired, say for diagnostic procedures. Longer-acting compounds are generally used for effecting longer-term reductions in intraocular pressure, such as is desired when treating chronic glaucoma. Thus, the method of the present invention provides a very useful therapeutic alternative for the treatment of glaucoma or for lowering intraocular pressure.

The rate of hydrolysis of the ester function of compounds of the present invention is influenced by the type of amine substituent. By varying the amine substituent it is possible to vary the length of duration of the compound in the body. The presence of the amine substituent also makes the compounds less lipophilic. Compounds that are less lipophilic have a reduced potential to cause central nervous system effects since there is less potential for CNS penetration.

The in vitro studies hereinafter described indicate that the compounds used in the method of the present invention will undergo different rates of enzymatic hydrolysis depending on their location within the body (see Table III). For example, compound I is completely hydrolyzed within 60 minutes in liver homogenate while only 7% hydrolyzed after two hours in aqueous humor. Compound III is more stable in aqueous humor, hydrolyzing 0.0% after one hour and 2.0% after two hours.

A. Beta Blocking Activity In Vitro

Several of the compounds of the present invention were tested for β-blocking activity in vitro using guinea pig right atria and guinea pig tracheal strips mounted in a tissue bath containing oxygenated (95% $O_2$-5% $CO_2$) Krebs physiological salt solution at 37° C. Each tissue was suspended between a fixed glass rod and a Statham Universal Transducer connected to a Beckman recorder. Atria were allowed to beat spontaneously under a loading tension of approximately 0.5 gm. Intrinsic depressant or stimulant activity was determined for each compound by progressively increasing concentrations in the tissue baths at 60-minute intervals. Tissues were not washed between increments. The maximum concentration showing little or no cardiodepressant activity was chosen for blockade experiments. Changes in rate in response to isoproterenol, a standard β-receptor agonist, were measured in the absence and presence of test compounds. Spiral strips of guinea pig trachea were suspended under 5 gm resting tension and incubated with phentolamine, tropolone and cocaine. Active tension was generated by addition of carbachol (3.0×10$^{-7}$M) and decreases in tension in response to isoproterenol were quantitated. Cumulative concentration-response curves were produced with isoproterenol both before and after 60-minute incubation of test compounds with atria and trachea. Compounds with β-blocking activity shifted concentration-response curves to the right. The blocking potency of test compounds was estimated by computing $pA_2$ values (-log $K_B$) by the method of Furchgott, the Pharmacological Differentiation of Adrenergic Receptors, *Ann. N.Y. Acad. Sci.*, 139: 553–570 (1967). Comparison of blockade of right atrial and tracheal responses to isoproterenol permits assessment of cardioselectivity of test compounds; i.e., cardioselective compounds are relatively more effective in blocking atrial rate than tracheal force response to isoproterenol. The degree of cardioselectivity was estimated from the ratio, $K_B$ trachea/$K_B$ atria ($10^{(pA_2\text{atria}-pA_2\text{trachea})}$). A ratio greater than one indicates cardioselectivity. Test drugs were dissolved in distilled water and added to the bath (30 ml) in a volume of 10 or 100 μl. The results of the in vitro tests are contained in Table I. All of the test compounds are active β-blockers.

TABLE I

| Compound of Example | Beta-Blocking Activity In Vitro | | Cardioselectivity |
|---|---|---|---|
| | $PA_2$ | | $K_B$(Trachea)/$K_B$(Atria) |
| | Rt. Atria | Trachea | |
| I | 7.3 | 7.0 | 2 |
| II | 8.1 | 7.5 | 4 |
| III | 8.3 | 7.7 | 4 |
| IV | 8.1 | 6.7 | 25 |
| IIIE | 7.6 | — | — |
| VI | >9.0 | — | — |
| VII | 6.8 | 7.1 | 2 |
| VIII | 8.7 | 8.8 | 0 |
| IIIA | 6.8 | 5.9 | 8 |
| IIID | >10.0 | — | — |
| VIIIA | 7.5 | — | — |
| IIIB | — | — | — |

B. Duration and Potency of Beta-Blocking Action in Vivo

The duration of β-blockade was determined In vivo using pentobarbital-anesthetized dogs instrumented for measurement of heart rate using a Beckman cardiotachometer triggered electronically by a phasic aortic blood pressure signal. Both vagus nerves were served in the cervical region and the animals were mechanically ventilated. The experimental design used employed a 3-hour infusion of test compound. Bolus doses of isoproterenol (0.5 μg/kg) were used to assess the degree of β-blockade and recovery from β-blockade after determination of the infusion. The doses were spaced at 10-minute intervals and were given before, during and following the infusion of test compounds. The infusion rate was adjusted so that at the end of the 3-hour infusion period the degree of isoproterenol inhibition averaged about 50% of control. Following termination of blocker infusion, percent recovery from β-blockade was computed and the time associated with 80% recovery estimated. The results are contained in Table II.

TABLE II

| Compound of Example | Beta-Blocking Activity In Vivo | | | | |
|---|---|---|---|---|---|
| | Potency (mg/kg/180 min) | Recovery Time (min) | | | |
| | | % 1$^a$ | 50% | 80% | N$^b$ |
| I | 3.0 | 54 ± 2 | 8 ± 1 | 18 ± 1 | 3 |
| II | 2.3 | 59 ± 2 | 7 ± 1 | 17 ± 1 | 5 |
| III | 0.6/1.1 | 57/60 | 20/19 | 40/45 | 2 |
| IV | 0.7 | 72 ± 3 | >60 | >60 | 3 |
| VI | 0.1 | 93/89 | >60 | >60 | 2 |
| VIII | 1.4 | 74 | 26 ± 6 | >60 | 3 |
| Propranolol | 0.225 | 67 ± 6 | >60 | >60 | 5 |

$^a$Percent inhibition of heart rate response to isoproterenol
$^b$Number of experiment

C. Enzymatic Hydrolysis of Beta-Blockers by Dog Blood, Liver Homogenate, and Aqueous Humor Chemicals—Acetonitrile was "HPLC" grade. Distilled water was used to dissolve the compounds and 0.01 N HCl was used to dissolve compounds requiring an acidic pH for dissolution.

Enzyme Source—Fresh aqueous humor was collected from eyes of dogs using a 23-gauge needle while fresh dog blood was collected into heparinized Vacutainer tubes. Fresh liver was homogenized in 0.9% NaCl using a Potter-Elvehjem Teflon pestle and glass homogenizer to make a 25% (W/V) homogenate.

Incubation Condition—A 0.5 ml aliquot of dog aqueous humor, blood, or liver homogenate was incubated with 12.5 μg (0.5 ml) of β-blocker in a Dubnoff shaking metabolic incubator at 37° C. for 60 and 120 min. Denatured tissue controls were prepared by adding 2.0 ml of acetonitrile into 0.5 ml of aqueous humor, blood, or liver homogenate to destroy esterase activities prior to addition of the β-blockers. These controls were then incubated at 37° C. for 120 min. After 60 and 120 min, the incubations were terminated by addition of 2 ml of acetonitrile and immediately mixed by a Vortex• to stop esterase activities.

Sample Processing and Data Analyses—All samples were centrifuged at 4000 RPM for 10 min to sediment denatured proteins. The resultant supernatants were transferred to WISP• vials and analyzed using an HPLC assay developed for beta blockers. The hydrolysis of β-blockers by aqueous humor, blood, and liver homogenate was determined by disappearance of the compounds. The extent of enzymatic hydrolysis by each tissue was determined by comparing the amount of each compound (absolute peak area) recovered at each time point to the amount of each compound (absolute peak area) in denatured tissue control and aqueous control samples. The results of these experiments are shown in Table III.

D. Half-Lives of Beta Blockers in Dog Whole Blood and Dog Liver Homogenate

The disappearance of the compounds of the present invention in vitro in human whole blood, dog whole blood, and dog liver homogenate is demonstrated by the following assay procedures: the rate of disappearance of a compound is expressed as the half-life ($T_{\frac{1}{2}}$), which is the time period in which one half of the initial amount of compound tested disappears. In each experiment, 1 ml of a solution containing 50 μg of the test compound was added to 1 ml of whole blood or 1 ml of a 33% (w/v) liver homogenate. The samples were incubated in a Dubnoff shaking metabolic incubator for 2.5, 5.0, 10.0, 20.0, 30.0 and 60.0 minutes at 37° C. At the designated time periods, the test mixtures were removed from the incubator and transferred to a 0° C. ice bath. Acetonitrile (2 ml) was immediately added and the mixtures were mixed to stop enzymatic hydrolysis. Zero time samples were prepared by adding 2 ml of acetonitrile to denature the proteins prior to addition of the test compounds. After centrifugation to sediment denatured proteins, 2 ml of the supernatant was removed and analyzed by high pressure liquid chromatography, using a mobile phase of 60% acetonitrile/40% 0.05 M sodium phosphate buffer (pH 6.6), a U.V. detector and Waters μ Bondapak Phenyl column.

The half life of each test compound was determined graphically by plotting the decrease in concentrations as a function of time. The results of the experiments are shown in Table III.

The present invention is further illustrated by the following examples which are not intended to be limiting.

leaving an oil which was dissolved in 100 ml of ethyl acetate/ethyl ether (1:1). The product crystallized slowly upon refrigeration to yield 1.8 g (11%) of product, which had a melting point of 115°–116° C. The IR and NMR spectra and elemental analysis were consistent with the assigned structure.

EXAMPLE II

This example describes the synthesis of a compound of the following formula:

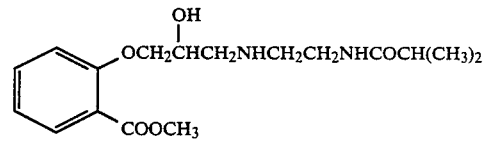

Methyl 2-[2-Hydroxy-3-[N-[2-(2-methylpropionamido)ethyl]amino]propoxy]benzoate The procedure of Example I was repeated in all essential details to produce the above compound, except that an equivalent amount of isopropylcarbonylethylenediamine was substituted for the acetylethylenediamine. The product, which was crystallized from methanol/ethyl ether, was identified by NMR and IR spectroscopy and by elemental analysis and had a melting point of 128°–129° C.

EXAMPLE III

This example describes the synthesis of a compound of the following formula:

TABLE III
| | STABILITY IN DOG BLOOD, LIVER HOMOGENATE AND AQUEOUS HUMOR | | | | | | | | |
|---|---|---|---|---|---|---|---|---|---|
| COMPOUND OF EXAMPLE | DOG BLOOD | | | DOG LIVER HOMOGENATE | | | DOG AQUEOUS HUMOR | | |
| | % 1 HR[a] | % 2 HR[a] | T½ min[b] | % 1 HR[a] | % 2 HR[a] | T½ min[b] | % 1 HR[a] | % 2 HR[a] | T½ min |
| I | 54 | 47 | 62 ± 8 | 0 | 0 | <<60[c], 167 | 93 | 93 | >>120[c] |
| II | 41 | 16 | 62 ± 3 | 0 | 0 | <<60[c], >180 | 94 | 91 | >>120[c] |
| III | 53 | 23 | 73 ± 16 | 0 | 0 | <<60[c], 129 | 100 | 98 | >>120[c] |
| IV | — | — | >180 | — | — | >180 | — | — | — |

[a]% Drug remaining—determined by procedure C
[b]Half-life determined by procedure D
[c]Approximate value—determined by procedure C

EXAMPLE I

This example describes the synthesis of a compound of the following formula.

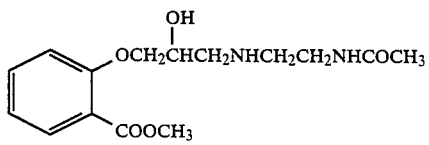

Methyl 2-[2-Hydroxy-3-[N-2-(-acetamidoethyl)amino]propoxy]benzoate 2.1 g of acetylethylenediamine (0.024 mole) and 5 of methyl 2-(2,3-epoxypropoxy)benzoate (0.024 mole) were reacted in methanol for 4 hours at 80° C. The methanol was then removed under reduced pressure,

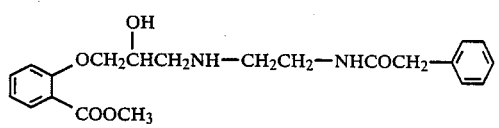

Methyl 2-[2-Hydroxy-3-[N-[2-(phenylacetamido)ethyl]amino]propoxy]benzoate

The procedure of Example I was repeated in all essential details to produce the above compound, except that an equivalent amount of benzylcarbonylethylenediamine was substituted for the acetylethylenediamine. The product, which was crystallized from ethyl acetate/ethyl ether, was identified by NMR and IR spectroscopy and by elemental analysis and had a melting point of 114°–115° C.

EXAMPLE IV

This example describes the synthesis of a compound of the following formula:

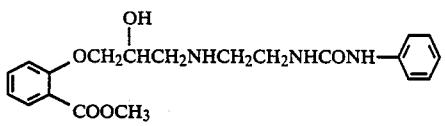

Methyl 2-[2-Hydroxy-3-[N-[2-[N-(phenylaminocarbonyl)amino]ethyl]amino]propoxy]benzoate 4.8 g of N-phenyl-N'-(2-aminoethyl)urea HCl salt (0.024 mole) was placed in 100 ml of methanol, and 2.5 g of triethylamine (0.024 mole) was added. While this reaction mixture was being stirred, a solution of 5 g of methyl 2-(2,3-epoxypropoxy)benzoate (0.024 mole) in 25 ml methanol was added slowly. The solution was then heated to reflux for 4 hours. The methanol was removed under reduced pressure and the resulting gel-like solid was dissolved in 100 ml of methylene chloride. The organic layer was washed twice with 100 ml of water and dried over anhydrous magnesium sulfate. Removal of the methylene chloride left an oil which was dissolved in 50 ml of methanol/ethyl ether (1:1) from which the product crystallized slowly upon refrigeration to afford 0.7 g (7.5%) of product having a melting point of 133°–134° C. The compound was identified by its NMR spectrum and elemental analysis.

EXAMPLE V

This example describes the synthesis of a compound of the following formula

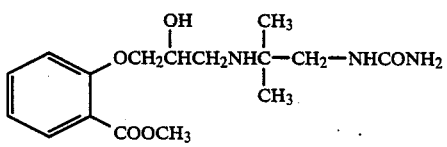

Methyl 2-[2-Hydroxy-3-[N-[1,1-dimethyl-2-(aminocarbonylamino)ethyl]amino]propoxy]benzoate A mixture of 3.17 g (0.0152 mole) of methyl 2-(2,3-epoxypropoxy)b-enzoate and 2.0 g (0.0152 mole) of 1,1-dimethyl-2-aminocarbonylamino)ethylamine was heated to reflux for 16 hours in 100 ml of methanol. The methanol was then removed under reduced pressure leaving an oil. The oil was dissolved in 10 ml of EtOAc and 50 ml of ether added. The oily mixture was stirred rapidly at 25° C. on a magnetic stirrer and 10 ml of isopropyl alcohol was added and the product crystallized gradually at room temperature. It was filtered and recrystallized from methanol:ether (1:3) to provide 2.8 g (55%) having a melting point of 62° C.

EXAMPLE VI

This example describes the synthesis of a compound of the following formula:

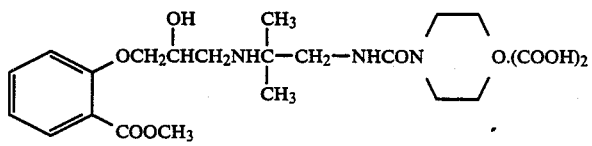

Methyl 2-[2-Hydroxy-3-[N-[1,1-dimethyl-2-(1-morpholinocarbonylamino)ethyl]amino]propoxy]benzoate Oxalate The procedure of Example IV was repeated in all essential details to produce the above compound, except that an equivalent amount of 1,1-dimethyl-2-(morpholinocarbonylamino)ethylamine was substituted for N-phenyl-N'-(2-aminoethyl)urea hydrochloride, and the final product was isolated as its oxalate salt. The product, which was crystallized from acetone/ethyl ether, was identified by NMR spectroscopy and elemental analysis and had a melting point of 113°–114° C.

EXAMPLE VII

This example describes the synthesis of a compound of the following formula:

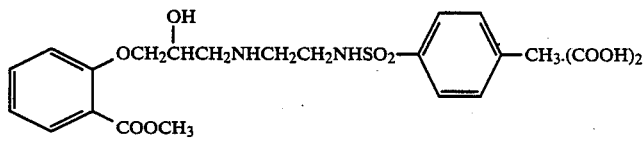

Methyl 2-[2-Hydroxy-3-[N-[2-[N-(4-methylphenylsulfonyl)amino]ethyl]amino]propoxy]benzoate Oxalate A solution of 2.15 g of N-(2-aminoethyl)-p-toluenesulfonamide (0.1 mole) and 2.08 g of methyl 2-(2,3-epoxypropoxy)benzoate (0.01 mole) in 100 ml of methanol was stored at 25° C. for 4 hours. The methanol was then removed under reduced pressure, leaving an oil (NMR indicated only mono-alkylated product). The oil was then dissolved in 50 ml of methanol and an equimolar quantity of oxalic acid was added to the solution. 50 Ml of acetone was added, and the product crystallized upon refrigeration. The product was recrystallized from acetone/methanol (1:1) to yield 1.4 g of product which had a melting point of 165°–166° C. The elemental analysis (CHN) and NMR spectrum were consistent with the assigned structure.

EXAMPLE VIII

This example describes the synthesis of a compound of the following formula:

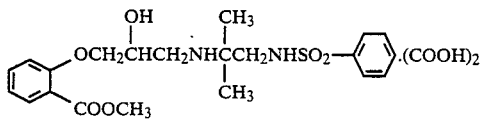

Methyl 2-[2-Hydroxy-3-[N-[1,1-dimethyl-2-(phenylsulfonylamino)ethyl]amino]proxy]benzoate Oxalate The procedure of Example VII was repeated in all essential details to produce the above compound, except that an equivalent amount of 1,1-dimethyl-2-(phenylsulfonylamino)ethylamine was substituted for N-(2-aminoethyl)-p-toluenesulfonamide and the reactants were heated in methanol to reflux for 16 hours. The product, which was crystallized from acetone/methanol, was identified by NMR spectroscopy and elemental analysis and had a melting point of 117°–118° C.

EXAMPLE IX

This example describes the synthesis of an intermediate amine of the following formula:

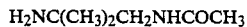

1,1-Dimethyl-2-acetamidoethylamine

A mixture of 26.4 g (0.3 mol) of ethyl acetate and 79.2 g (0.9 mole) of 1,2-diamino-2-methylpropane was heated at 100° C. in a pressured bomb for 36 hours. The reaction mixture was evaporated in vacuo and distilled to give 22.4 g (57.4%) of product which had a boiling point of 100° C. at 0.1 mmHg. This product was identified by NMR and IR spectroscopy.

EXAMPLE X

This example describes the synthesis of an intermediate amine of the following formula:

NH₂CH₂CH₂NHCOCH(CH₃)₂

2-(2-Methylpropionamido)ethylamine

The procedure of Example IX was repeated in all essential details to produce the above compound, except that equivalent amounts of ethylenediamine and ethyl 2,2-dimethylacetate were substituted for 1,2-diamino-2-methylpropane and ethyl acetate, respectively. The product, which was identified by NMR and IR spectroscopy, was recovered as an oil.

EXAMPLE XI

This example describes the synthesis of an intermediate amine of the following formula:

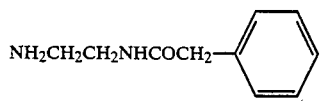

2-(Phenylacetamido)ethylamine

The procedure of Example IX was repeated in all essential details to produce the above compound, except that equivalent amounts of ethylenediamine and ethyl phenylacetate were substituted for 1,2-diamino-2-methylpropane and ethyl acetate, respectively. The product, which was identified by NMR and IR spectroscopy, had a melting point of 37°–38° C.

EXAMPLE XII

This example describes the synthesis of an intermediate amine of the following formula:

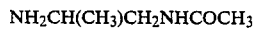

1-Methyl-2-acetamidoethylamine

The procedure of Example IX was repeated in all essential details to produce the above compound, except that an equivalent amount of 1,2-diaminopropane was substituted for 1,2-diamino-2-methylpropane. The product, which was identified by NMR and IR spectroscopy, had a boiling point of 90°–95° C. at 0.1 mmHg.

EXAMPLE XIII

This example describes the synthesis of an intermediate amine of the following formula:

NH₂CH₂CH₂NHCOCH₃

1-Acetamidoethylamine

The procedure of Example IX was repeated in all essential details to produce the above compound, except that an equivalent amount of ethylenediamine was substituted for 1,2-diamino-2-methylpropane. The product, which was identified by NMR and IR spectroscopy, had a melting point of 51°–52° C.

EXAMPLE XIV

This example describes the synthesis of an intermediate amine of the following formula:

1,1-Dimethyl-(2-methylpropionamido)ethylamine

The procedure of Example IX was repeated in all essential details to produce the above compound, except that an equivalent amount of ethyl 2,2-dimethylacetate was substituted for ethyl acetate. The product, which was identified by NMR and IR spectroscopy, had a boiling point of 110° C. at 0.1 mmHg.

EXAMPLE XV

This example describes the synthesis of an intermediate amine of the following formula:

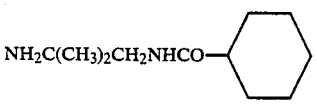

1,1-Dimethyl-2-(cyclohexylcarbonylamino)ethylamine

The procedure of Example IX was repeated in all essential details to produce the above compound, except that an equivalent amount of ethyl cyclohexylcarboxylate was substituted for ethyl acetate. The product, which was identified by NMR and IR spectroscopy, had a melting point of 100°–110° C.

EXAMPLE XVI

This example describes the synthesis of an intermediate amine of the following formula:

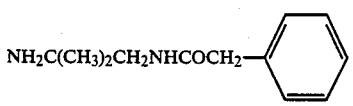

NH₂C(CH₃)₂CH₂NHCOCH₂—

1,1-Dimethyl-2-(phenylacetamido)ethylamine

The procedure of Example IX was repeated in all essential details to produce the above compound, except that an equivalent amount of ethyl phenylacetate was substituted for ethyl acetate. The product, which was identified by NMR and IR spectroscopy, had a melting point of 46° C.

EXAMPLE XVII

This example describes the synthesis of an amine of the following formula:

H₂NC(CH₃)₂CH₂NHCOOC₂H₅

1,1-Dimethyl-2-(ethoxycarbonylamino)ethylamine

To a mixture of 88.2 g (1 mol) of 1,2-diamino-2-methylpropane, 50 ml of triethylamine and 500 ml of diethylether was added dropwise a solution of 27.1 g (0.25 mol) of ethyl chloroformate in 100 ml of ether. The reaction mixture was stirred for 16 hours at 25° C. and filtered. Evaporation of the filtrate to dryness gave 38 g (95%) of product which was identified by NMR and IR spectroscopy.

EXAMPLE XVIII

This example describes the synthesis of an amine of the following formula:

H₂NC(CH₃)₂CH₂NHCONHCH₃

1,1-Dimethyl-2-(methylaminocarbonylamino)ethylamine

A mixture of 5.7 g (0.1 mol) of methyl isocyanate and 20 ml of pyridine was stirred at 0° C. for 5 minutes and then slowly added to a solution of 20 g (0.23 mol) of 1,2-diamino-2-methylpropane in 30 ml of pyridine. The reaction mixture was warmed to 20° C. and stirred for 1 hour. Evaporation of the solvent in vacuo gave 11.6 g (90%) of product, recovered as an oil, which was identified by NMR and IR spectroscopy.

EXAMPLE IXX

This experiment describes the synthesis of an amine of the following formula:

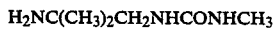

H₂NC(CH₃)₂CH₂NHCONH₂

1,1-Dimethyl-2-(aminocarbonylamino)ethylamine

The procedure of Example XVIII was repeated in all essential details, except that an equivalent amount of cyanic acid was used instead of methylisocyanate as starting material to afford the product which was recovered as a semi-solid.

Alternatively, the urea of this example was prepared as follows:

A mixture of 26.5 g (0.2 mole) of 1,2-diamino-2-methylpropane and 18 g (0.2 mole) of urea in 150 ml of water was refluxed for 4 h. The mixture was concentrated under reduced pressure. The residue was stirred with chloroform, then filtered, and the filtrate was concentrated to a solid, which was recrystallized from ethyl acetate to provide 15 g (38%) of product which had a melting point of 87°–90° C. The IR and NMR spectra were consistent with the assigned structure.

EXAMPLE XX

This example describes the synthesis of an amine of the following formula:

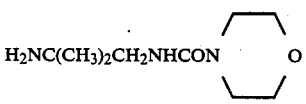

H₂NC(CH₃)₂CH₂NHCON   O 1,1-Dimethyl-2-(morpholinocarbonylamino)ethylamine

To 16.2 g (0.1 mol) of N,N'-carbonyldiimidazole in 100 ml of chloroform was added 8.7 g (0.1 mol) of morpholine. The reaction mixture was stirred for 30 minutes at 25° C. and slowly added to a solution of 1,2-diamino-2-methylpropane in 100 ml of chloroform. After stirring for 30 minutes, the reaction was evaporated to dryness and the product was chromatographed on silica gel/ethanol-ethyl ether (1:1) to give 8.74 g (43%) of product which was recovered as a semi-solid. The NMR and IR spectra were consistent with the assigned structure.

EXAMPLE XXI

This example describes the synthesis of an amine of the following formula:

H₂NC(CH₃)₂CH₂NHCONH—

1,1-Dimethyl-2-(phenylaminocarbonylamino)ethylamine

The procedure of Example XX was repeated in all essential details to provide the above compound, except that an equivalent amount of aniline was substituted for morpholine. The product, which was identified by NMR and IR spectroscopy, had a melting point of 130°–131° C.

EXAMPLE XXII

This example describes the synthesis of an amine of the following formula:

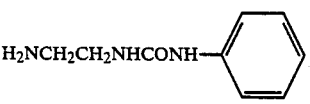

H₂NCH₂CH₂NHCONH—

2-(Phenylaminocarbonylamino)ethylamine

To a stirring suspensions of 0.057 mole of acetylethylene diamine in 100 ml of methylene chloride at 10° C.

was added dropwise 0.057 mole of phenyl isocyanate. Soon after the addition a solid precipitated. 100 ml of anhydrous ether was added to the reaction mixture and stirring was continued for another 30 minutes. The solid was recovered by filtration, dissolved in 50 ml of 15% hydrochloric acid, and the solution was heated to 80° C. for 4 hours. Removal of the aqueous acid afforded the product which had a melting point of 190.4° C.

EXAMPLE XXIII

This example describes the synthesis of an amine of the following formula:

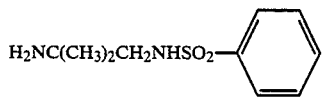

1,1-Dimethyl-2-(phenylsulfonylamino)ethylamine

To a mixture of 14.97 g (0.196 mol) of 1,2-diamino-2-methyl-propane in 300 ml of chloroform and 80 ml pyridine at 0° C. was added 10 g (0.057 mol) of benzenesulfonyl chloride at 0° C. The reaction mixture was stirred at 0° C. for 30 minutes and allowed to reach room temperature. The mixture was evaporated to dryness in vacuo and the residue was partitioned between water and chloroform. Evaporation of the chloroform gave 10.3 g (79%) of semisolid. The product was identified by NMR and IR spectroscopy and elemental analysis.

EXAMPLE XXIV

This example describes the preparation of the following compound:

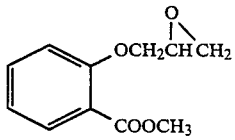

EXAMPLE XXV

The procedure of Example I is repeated in all essential details except that an appropriate amine is substituted for the acetylethylene diamine to provide the compounds described in the following table:

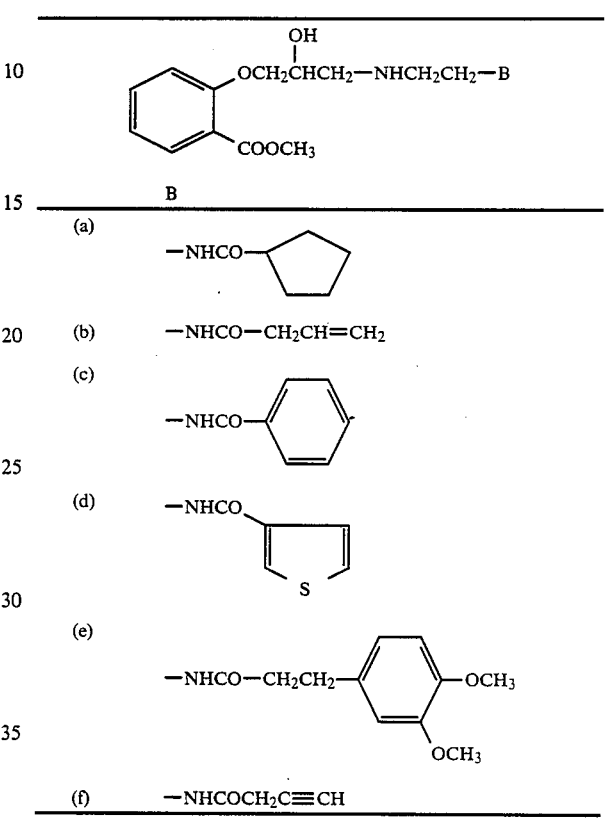

EXAMPLE XXVI

This example describes the synthesis of a compound of the following formula:

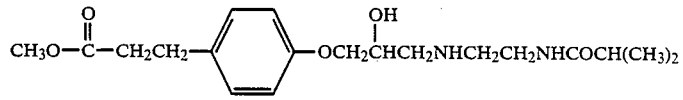

(a) Methyl 3-(4-Hydroxyphenyl)propionate

A solution of 17 gm (0.1 mole) of 3-(4-hydroxyphenyl) propionic acid in 500 ml methanol and 2 ml concentrated sulfuric acid was placed in a Soxhlet extractor charged with 3A molecular sieves. The solution was heated to reflux for 72 hours and the sieves were exchanged at 24 hour intervals. The reaction medium was then evaporated to an oil which was dissolved in 100 ml toluene and extracted with 3 × 100 ml water. The toluene phase was dried over magnesium sulfate, treated with activated charcoal and evaporated to provide 15 gm (80%) of a clear oil. The NMR spectrum was consistent with the assigned structure and this material was utilized directly in the next reaction step.

Methyl 2-(2,3-Epoxypropoxy)benzoate

A mixture of 15.2 g (0.10 mole) of methyl 2-hydroxybenzoate, 27.6 g (0.20 mole) of potassium carbonate and 31 ml (0.40 mole) of epichlorohydrin in 250 ml of acetone was heated to reflux for 24 hours. The reaction medium was then filtered and evaporated under reduced pressure. The resulting oil was dissolved in 100 ml of toluene and washed consecutively with 100 ml of water, 2 × 100 ml of 1.0N sodium hydroxide and 2 × 100 ml of water. The organic phase was then dried over magnesium sulfate and evaporated under reduced pressure to provide the crude product as an oil. Purification was effected by vacuum distillation to provide an oil in 12% yield: boiling point 148° C. (75μ). The NMR and IR spectra and elemental analysis were consistent with the assigned structure.

(b) Methyl 3-[4-(2,3-Epoxypropoxy)phenyl]propionate

The oil described above was utilized directly in the condensation reaction with epichlorohydrin, potassium carbonate, and acetone as described in Example XXIV. Purification was effected by vacuum distillation (156°; 0.4 mm pressure) and provided the aryl ether epoxide in 45% yield. The NMR spectrum and the elemental analysis were consistent with the assigned structure.

(c) Methyl 3-[4-[2-Hydroxy-3-[N-[2-(methylpropionamido)ethyl]amino]-propoxy-]phenyl]propionate A mixture of 2.4 g (0.01 mole) of methyl 3-[4-(2,3-epoxypropoxy)-phenyl]propionate and 2.6 g (0.02 mole) of 2-(2-methylpropionamido)-ethylamine in 25 ml of methanol was heated to reflux for 4 hr. The methanol was removed under reduced pressure to afford a dark oil which was dissolved in 100 ml of ethyl acetate and washed with 50 ml of water. The organic phase was separated, dried over magnesium sulfate, concentrated under reduced pressure and cooled to 0°–2° C. to afford a crystalline product. An additional recrystallization from ethyl acetate provided 0.8 (22%) of product which melted at 100°–102° C. The IR and NMR spectra and elemental analysis were consistent with the assigned structure.

EXAMPLE XXVII

This example describes the synthesis of a compound of the following formula:

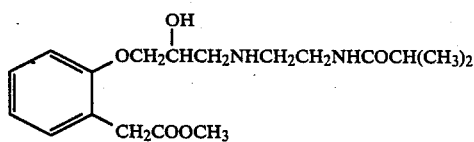

(a) Methyl (2-Hydroxyphenyl)acetate

A solution of 15 gm (0.1 mole) of 2-hydroxyphenylacetic acid in 500 ml methanol and 2 ml concentrated sulfuric acid was placed in a Soxhlet extractor charged with 3A molecular sieves. The solution was heated to reflux for 72 hours, and the sieves were exchanged at 24-hour intervals. The reaction medium was then evaporated to an oil which was dissolved in 100 ml tolene and extracted with 3×100 ml portions of water. The toluene phase was dried over magnesium sulfate, treated with activated charcoal and evaporated to provide 13 gm (80% yield) of a yellow oil. The NMR spectrum was consistent with the assigned structure and this material was used in the next reaction step.

(b) Methyl 2-(2,3-Epoxypropoxy)phenylacetate

The oil described in the preceding reaction was utilized directly in the condensation reaction with epichlorohydrin, potassium carbonate and acetone as described in Example XXIV to provide the desired aryl ether epoxide in 60% yield. The NMR spectrum of the clear oil obtained in this manner was consistent with the assigned structure.

(c) Methyl 2-[2-Hydroxy-3-[N-[2-(methylpropionamido)ethyl]amino]-propoxylphenyl]acetate A mixture of 5.0 g (0.02 mole) of methyl 2-(2,3-epoxypropoxy)-phenylacetate and 2.93 g (0.02 mole) of 2-(2-methylpropionamido)ethylamine in 200 ml of methanol, was heated to reflux for 4 hr. The mixture was concentrated under reduced pressure to afford a dark brown oil which was then stirred with 100 ml of ether for 15 min. to yield an off-white solid. The product was collected by filtration, washed with ether and recrystallized three times from ethyl acetate to provide 0.7 g (9%) of white crystals, which melted at 109°–111° C. The IR and NMR spectra and elemental analysis were consistent with the assigned structure.

EXAMPLE XXVIII

This example describes the synthesis of a compound of the following formula:

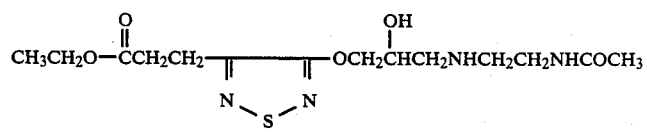

Methyl 3-[4-[2-Hydroxy-3-(2-acetylaminoethylamino)propoxy]-3-[1,2,5-thiadiazolyl]]propionate The procedure of Example XXVI(c) is repeated in all essential details to produce the above compound, except that an equivalent amount of methyl 3-[4-(2,3-epoxypropoxy)-3-[1,2,5-thiadiazolyl]]propionate is substituted for 3-[4-(2,3-epoxypropoxy)phenyl]propionate.

EXAMPLE XXIX

This example describes the synthesis of a compound of the following formula:

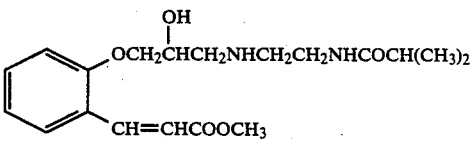

(a) Methyl 2-Hydroxycinnamate

A solution of 200 g (1.218 mole) of 2-hydroxycinnamic acid in 2L of anhydrous methanol was treated with 10 drops of concentrated sulfuric acid. This solution was refluxed for 72 hr., using a Soxhlet extractor charged with 200 g of 3A molecular sieves. The methanolic solution was then concentrated under reduced pressure and cooled to afford 200 g (92%) of white crystals, which were used directly in the next step without additional purification.

(b) Methyl 2-(2,3-Epoxypropoxy)cinnamate

A mixture of 200 g (1.12 mole) of methyl 2-hydroxycinnamate and 300 g (1.68 mole) of potassium carbonate in 2L of acetone was treated with 311 g (3.36 moles) of epichlorohydrin. The mixture was stirred and heated to reflux for 48 hr. The reaction medium was filtered and concentrated under reduced pressure to leave a brown oil. Ether was added and a small amount of insoluble material was removed by filtration. The filtrate was concentrated under reduced pressure to give 230 g (87%) of crude epoxide. The NMR spectrum of this material was consistent with the assigned structure and it was used directly in the next step without additional purification.

(c) Methyl 2-[2-Hydroxy-3-[N-X[2-(methylpropionamido)ethyl-]amino]-propoxy]cinnamate A mixture of 23.4 g (0.1 mole) of methyl 2-(2,3-epoxypropoxy)-cinnamate and 13.0 g (0.1 mole) of 2-(2-methylpropionamido)ethylamine in 200 ml of methanol was stirred at room temperature for 16 hr. The mixture was then concentrated under reduced pressure to provide an oil, which slowly crystallized. The solid was recrystallized from acetone:ether (1:4) to afford 13.6 g (37%) of product which melted at 143.8° C. The IR and NMR spectra and elemental analysis were consistent with the assigned structure.

EXAMPLE XXX

This example describes the synthesis of a compound of the following formula:

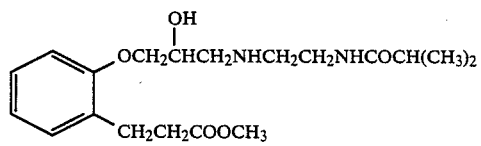

Methyl 3-[2-[2-Hydroxy-3-[N-[2-(methylpropionamido)ethyl-]amino]-propoxy]phenyl]propionate A solution of 3.0 g (0.008 mole) of methyl 2-[2-hydroxy-3-[N-[2-(methylpropionamido)ethyl]amino]-propoxy]cinnamate in 100 ml of methanol was treated with 0.3 g of 10% Pd-C catalyst and hydrogenated at 40 psi until no further uptake of hydrogen was observed (about 48 hr.). The catalyst was removed by filtration and the filtrate concentrated under reduced pressure to a solid, which was recrystallized from methanol:ether to provide 2.5 g (83%) of product, having a melting point of 119°-120° C. The IR and NMR spectra and elemental analysis were consistent with the assigned structure.

EXAMPLE XXXI

This experiment describes the synthesis of a compound of the following formula:

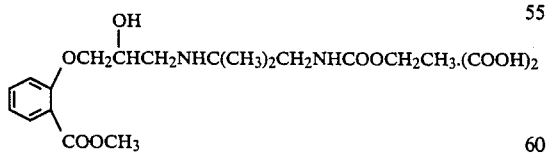

Methyl 2-[2-Hydroxy-3-[N-[2-[1,1-dimethyl-2-(ethoxycarbonylamino)]ethyl]amino]propoxy]benzoate Oxalate A solution of 5.0 g (0.03 mole) of 1,1-dimethyl-2-(ethoxycarbonylamino)ethylamine and 6.5 g (0.03 mole) of methyl 2-(2,3-epoxypropoxy)benzoate in 100 ml of dimethylformamide was heated at 70° for 24 hr. The solution was then cooled and diluted with 900 ml of ether. Hydrogen chloride gas was bubbled into the solution to precipitate an oil. The solvent was decanted and the oil was washed twice with ether and then dissolved in water. The aqueous solution was shaken with 150 ml of methylene chloride in a separatory funnel, separated, and made basic with sodium hydroxide. The resulting insoluble oil was extracted into ether, washed with water and dried over magnesium sulfate. Concentration of the solution under reduced pressure gave 3.4 g of an oil. The oil was taken up in 50 ml of methanol and added to an equivalent amount (1.2 g) of oxalic acid dissolved in methanol. The crystalline oxalate salt was finally produced in 25% yield by triturating with ether and cooling. The IR and NMR spectra and elemental analysis were consistent with the assigned structure.

EXAMPLE XXXII

This example describes the synthesis of a compound of the following formula:

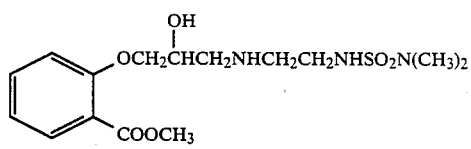

(a) 2-[N-[(Dimethylamino)sulfonyl]amino]ethylamine Hydrochloride

A solution of 14.3 g (0.1 mole) of dimethylsulfamyl chloride in 50 ml of methylene chloride was added dropwise to a rapidly stirred solution of 10.2 g (0.1 mole of N-acetylethylenediamine and 10.1 g (0.1 mole) of triethylamine in 150 ml of methylene chloride at 25° C. After the addition, the solution was stirred for 30 min and then washed in a separatory funnel with two 100 ml portions of water. The organic phase was separated, and dried over magnesium sulfate, and then concentrated under reduced pressure to afford N-[2-[(dimethyllamino)sulfonyl]-amino]ethyl]acetamide as an oil. The N-acetyl group was then removed by treatment of the oil with 100 ml of 15% HCl at 80° C. for 6 hr. This solution was concentrated under reduced pressure to provide 12.6 g (75%) of the product as an oil. The NMR spectrum was consistent with the assigned structure. The oil was used directly in the next step without additional purification.

(b) N-Benzylidene-2-[N'-[(dimethylamino)sulfonyl-]amino]ethylamine Hydrochloride A mixture of 4.0 g (0.02 mole) of 2-[N-[(dimethylamino)sulfonyl]-amino]ethylamine hydrochloride and 2.0 g (0.02 mole) of benzaldehyde was stirred and treated immediately with 2.0 g (0.02 mole) of triethylamine, followed by the addition of 200 ml of dry benzene. The solution was heated to reflux employing a Dean-Stark apparatus. After 2 hr at reflux, the benzene solution was cooled and washed twice with 100 ml portions of water. The organic phase was separated, dried over magnesium sulfate, and concentrated under reduced pressure to an oil, which was dissolved in ether and treated with HCl gas to precipitate a yellowish solid. The product was collected by filtration, washed with ether and air dried to provide 2.4 g (50%) of product. The NMR spectrum was consistent with the assigned structure and the solid was used without additional purification.

(c) N-Benzyl-2-[N'-[(dimethylamino)sulfonyl]amino]ethylamine Hydrochloride

A solution of 3.0 g (0.011 mole) of N-benzylidene-2-[N'-[(dimethylamino)sulfonyl]amino]ethylamine hydrochloride in 100 ml of methanol was hydrogenated, at 40 psi, over 0.3 g of 10% Pd-C catalyst until hydrogen uptake ceased (20 min.). The mixture was filtered and concentrated under reduced pressure to provide 3.0 g of crude product. The NMR spectrum was consistent with the assigned structure and the crude product was utilized directly without further purification.

(d) Methyl 2-[2-Hydroxy-3[N-benzyl-2[[N'-[(dimethylamino)sulfonyl]-amino]ethyl]amino]propoxy]benzoate Hydrochloride A solution of 3.0 g (0.011 mole) of N-benzyl-2-[(N'-[dimethylamino)sulfonyl]amino]ethylamine hydrochloride, 2.08 g (0.01 mole) of methyl 2-(2,3-epoxypropoxy)-benzoate and 1.01 g (0.01 mole) of triethylamine in 100 ml of methanol was heated to reflux for 4 hr. The solvent was removed under reduced pressure and the resulting oil was dissolved in methylene chloride and washed twice with 100 ml portions of water. The organic layer was separated, dried over magnesium sulfate and concentrated under reduced pressure to provide 2.5 g (50%) of product as an oil. The NMR spectrum was consistent with the assigned structure.

(e) Methyl 2-[2-Hydroxy-3-[N-[2-(dimethylamino)sulfonylamino]ethyl]-amino]propoxy]benzoate Hydrochloride A solution of 2.5 g (0.0054 mole) of the N-benzyl compound in 100 ml of methanol was hydrogenated at 45 psi over 0.3 g of 10% Pd-C catalyst until uptake of hydrogen ceased (about 20 min.). The mixture was filtered and concentrated under reduced pressure to afford an oil, which was crystallized from methanol: acetone:ether. This solid was recrystallized from acetone:ether (1:1) to provide 1.6 g (72%) of product, which had a melting point of 143° C. The IR and NMR spectra and elemental analysis were consistent with the assigned structure.

EXAMPLE XXXIII

This example describes the synthesis of a compound of the following formula:

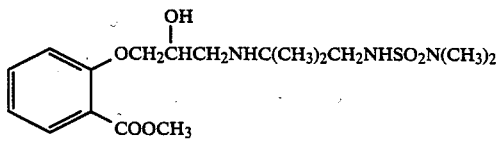

(a) [1,1-Dimethyl-2-[(dimethylamino)sulfonylamino]ethyl]amine

A mixture of 30.7 g (0.35 mole) of 1,2-diamino-2-methylpropane, 150 ml of ether and 50 ml of triethylamine was cooled to 0° C. and 20 g (0.14 mole) of dimethylsulfamoylchloride was added slowly. The mixture was stirred for 30 min. and then concentrated under reduced pressure. The residue was mised with water, basified with potassium carbonate and concentrated to dryness. Acetone was added and insoluble material was removed by filtration. Concentration of the filtrate gave a solid, which crystallized from toluene to give 16.5 g (60%) of product, m.p. 77°–78° C. The IR and MNR spectra were consistent with the assigned structure.

(b) Methyl 2-[2-Hydroxy-3-[1,1dimethyl-2[[(dimethylamino)sulfonylamino]ethyl]amino]propoxy]benzoate Hydrochloride The procedure of Example VII is repeated in all essential details to produce the above compound, except that an equivalent amount of 1,1-dimethyl-2-[(dimethylamino)sulfonylamino]ethyl]amine is substituted for N-(2-aminoethyl)-p-toluene sulfonamide.

EXAMPLE XXXIV

This example describes the synthesis of an amine of the following formula:

1,1-Dimethyl-2-(methoxyethoxycarbonyl)aminoethylamine

To 10 g (0.002 mole) of N,N'-carbonyldiimidazole, in 100 ml of methylene chloride, was added 4.7 g (0.062 mole) of 2-methoxyethanol. The reaction mixture was stirred at 25° C. for one hour and then 10.9 g (0.124 mole) of 1,2-diamino-2-methylpropane was added. The mixture was stirred for 18 hr. and then concentrated under reduced pressure. The crude product was chromatographed on silica gel. Elution with ethanolethylacetate (1:1) gave 9.1 g (80.5%) of product. The IR and NMR spectra were consistent with the assigned structure.

EXAMPLE XXXV

This example describes the synthesis of an amine of the following formula:

1,1-Dimethyl-2-(methylsulfonylamino)ethylamine

The procedure of Example XXIII was repeated in all essential details to provide the above compound, except that an equivalent amount of methane sulfonyl chloride was substituted for benzene sulfonyl chloride.

EXAMPLE XXXVI

This example describes the synthesis of a compound of the following formula:

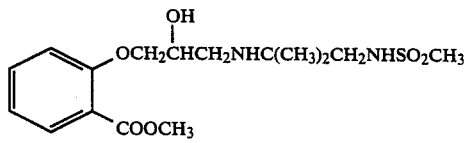

Methyl 2-[2-Hydroxy-3-[1,1-dimethyl-2-(methylsulfonylamino)ethyl]-amino]propoxy]benzoate The procedure of Example VII is repeated in all essential details to provide the above compound, except that an equivalent amount of 1,1-dimethyl-2-(methylsulfonylamino)ethylamine is substituted for N-(2-aminoethyl)-p-toluenesulfonamide.

EXAMPLE XXXVII

The procedure of Example VII is repeated in all essential details except that an appropriate amine is substituted for N-(2-aminoethyl)-p-toluenesulfonamide to provide the compounds described in the following table.

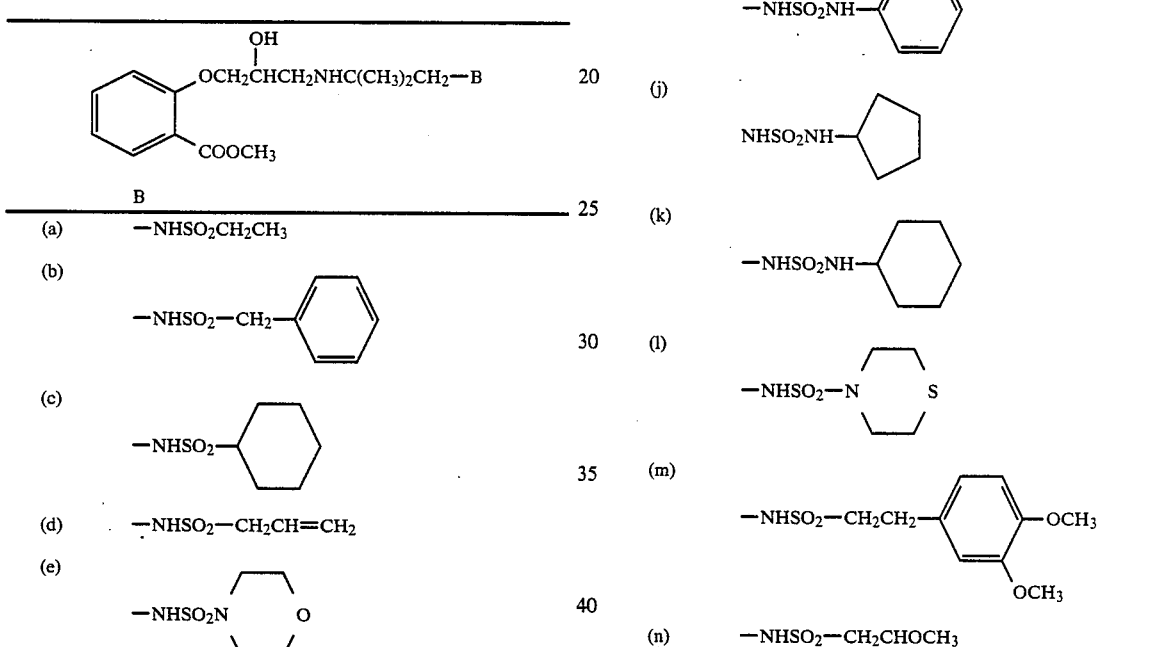

Using the method of the foregoing examples, the compounds listed in Table IV were made.

TABLE IV
Structures, Chemistry Experimental, and Pharmalogical Data

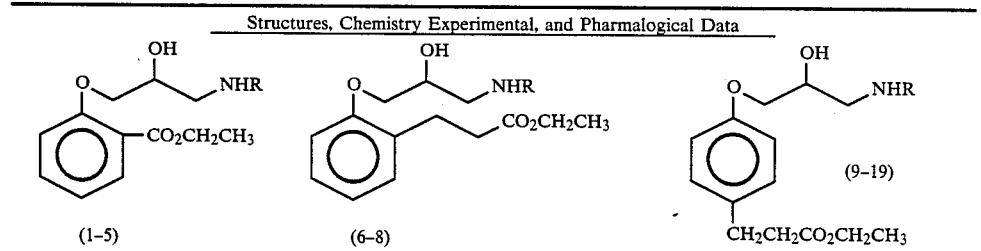

| No. | R | Formula[a] | mp °C. | In-Vivo $pA_2$[b] Trachea | Atria | In-Vitro[c] Duration | Local Apes[d] $ED_{50}$ |
|---|---|---|---|---|---|---|---|
| 1 | $CH_2CH_2NHCOCH(CH_3)_2$ | $C_{18}N_{28}N_2O_5$ | 83–4 | 7.7 | 8.5 | 48 ± 9 | 2.0 (1.4–3.3) |
| 2 | $C(CH_3)_2CH_2NHCO_2C_2H_5$ | $C_{19}H_{30}N_2O_6.(CO_2H)_2$ | 98–102 | 8.0 | 8.3 | 20 | 0.2 (0.1–0.4) |
| 3 | $C(CH_3)_2NHSO_2N(CH_3)_2$ | $C_{18}H_{31}N_3O_6S.0.5(CO_2H)_2.H_2O$ | 108–9 | 9.2 | 8.1 | 34 | 1.1 (0.5–1.9)[e] |
| 4 | $CH_2CH_2NHSO_2N(CH_3)_2$ | $C_{16}H_{27}N_3O_6S.HCl$ | 79–80 | 7.7 | 7.4 | 10 ± 3 | 10.0 (5.6–24.4) |
| 5 | $CH_2CH_2NHSO_2Ph(p\text{-}Me)$ | $C_{21}N_{28}N_2O_6S.0.5(CO_2H)_2.0.25H_2O$ | 99–102 | 7.6 | 6.8 | 14 | 1[f] |
| 6 | $CH_2CH_2NHCOCH(CH_3)_2$ | $C_{20}H_{32}N_2O_5.0.5H_2O$ | 108–9 | 7.7 | 7.2 | 42 ± 14 | 13.2 (8.9–21.9) |
| 7 | $CH_2CH_2NHSO_2N(CH_3)_2$ | $C_{18}H_{30}N_3O_6S.HCl$ | 104–5 | 7.9 | 8.2 | 26 ± 2 | 21.3 (16.7–29.9) |
| 8 | $CH_2CH_2NHSO_2Ph(p\text{-}Me)$ | $C_{23}N_{32}N_2O_6S.$ | 148–50 | 6.9 | 6.1 | — | 1[e] |

TABLE IV-continued
Structures, Chemistry Experimental, and Pharmalogical Data

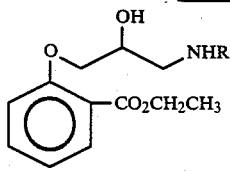
(1-5)

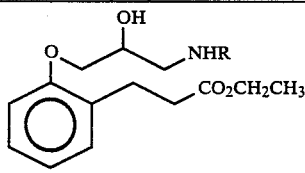
(6-8)

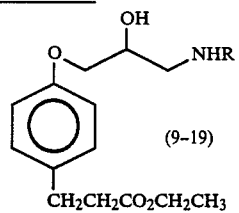
(9-19)
CH₂CH₂CO₂CH₂CH₃

| No. | R | Formula[a] | mp °C. | In-Vivo pA$_2$[b] Trachea | In-Vivo pA$_2$[b] Atria | In-Vitro[c] Duration | Local Apes[d] ED$_{50}$ |
|---|---|---|---|---|---|---|---|
| 9 | CH$_2$CH$_2$NHCOCH$_3$ | C$_{18}$N$_{28}$N$_2$O$_5$ (CO$_2$H)$_2$ | 82-3 | 6.5 | 6.3 | 10 ± 4 | >10 |
| 10 | CH$_2$CH$_2$NHCOCH(CH$_3$)$_2$ | C$_{20}$H$_{32}$N$_2$O$_5$ | 151-3 | 6.4 | 6.1 | 6 ± 3 | >10 |
| 11 | C(CH$_3$)$_2$CH$_2$NHCOC$_6$H$_{11}$ | C$_{25}$H$_{40}$N$_2$O$_5$·(CO$_2$H)$_2$ | 105-5 | 6.4 | — | — | >30 |
| 12 | CH$_2$CH$_2$NHCOCH$_2$Ph | C$_{24}$H$_{32}$N$_2$O$_5$ | 91-2 | 5.9 | 7.5 | 6 ± 4 | >30 |
| 13 | C(CH$_3$)$_2$CH$_2$NHCONH$_2$ | C$_{19}$H$_{31}$N$_3$O$_5$·(CO$_2$H)$_2$·0.5H$_2$O | 68-9 | 6.4 | 6.0 | 12 ± 4 | >30 |
| 14 | C(CH$_3$)$_2$CH$_2$NHCO$_2$C$_2$H$_5$ | C$_{21}$H$_{34}$N$_2$O$_6$·0.5(CO$_2$H)$_2$ | 132-4 | 6.7 | 6.1 | — | 11.9 (6.7->30) |
| 15 | C(CH$_3$)$_2$CH$_2$NHSO$_2$N(CH$_3$)$_2$ | C$_{20}$H$_{35}$N$_3$O$_6$S·0.5(CO$_2$H)$_2$·0.5H$_2$O | 147-9 147-9 | 6.5 6.5 | 5.8 5.8 | — — | >10 >10 |
| 16 | CH$_2$CH$_2$NHSO$_2$N(CH$_3$)$_2$ | C$_{18}$H$_{30}$N$_3$O$_6$S·HCl | 106-7 | 5.7 | 5.8 | — | 5.8 (3.8-9.1) |
| 17 | CH$_2$CH$_2$NHSO$_2$Ph(p-Me) | C$_{23}$H$_{32}$N$_2$O$_6$S·(CO$_2$H)$_2$ | 144-8 | 5.2 | 6.0 | — | >15 |
| 18 | C(CH$_3$)$_2$CH$_2$NHSO$_2$Ph | C$_{24}$H$_{34}$N$_2$O$_6$S·(CO$_2$H)$_2$ | 77-9 | 6.6 | 6.3 | — | >10 |
| 19 | C(CH$_3$)$_2$CH$_2$NHCON⌐O⌐ (morpholine) | C$_{23}$H$_{37}$N$_3$O$_6$ | 95-8 | 6.7 | 7.8 | 21 ± 4 | >30 |
| 20 | Propranolol | — | — | 8.9 | 8.7 | >60 | 0.3 (0.2 -0.7) |
| 21 | Timolol | — | — | — | 8.9 | >60 | >30 |

[a] All NMR spectral and elemental analyses data were in accord with the assigned structures.
[b] Number of experiments is equal to or greater than two for each compound. Tabulated pA$_2$ data are mean values. The range for each value is equal to or less than ± 0.2 units.
[c] Time in minutes for 50% recovery from 50% blockade levels after 3 h Infusions of drug. Number of experiments is equal to or greater than three for each compound unless noted otherwise. Tabulated data are mean values ± SEM. In general, the In vivo potencies paralleled the relationships observed in vitrol.
[d] Drug concentration (with 95% confidence Intervals) which produces half-maximal corneal anesthesis.
[e] Compound showed extreme ocular toxicity as well as anesthesia.
[f] Inadequate aqueous solubility precluded assessment of EC$_{50}$ value.

The following procedure is utilized to synthesis compounds similar to the compound of Example XXVIII to thereby provide the compounds described in the following tables.

```
        O
        ||
CH₃CH₂O—CCH₂CH₂—[thiadiazole]—OH
    1              N    N
                    \\S//
        ↓
        O
        ||
CH₃CH₂O—CCH₂CH₂—[thiadiazole]—OCH₂CH—O
    2              N    N         \\ //
                    \\S//          CH₂
        ↓
        O                        OH
        ||                       |
CH₃CH₂O—CCH₂CH₂—[thiadiazole]—OCH₂CHCH₂NHR
                   N    N
                    \\S//
```

EXAMPLE XXXVIII

Ethyl 3-[3-Hydroxy-1,2,5-thiadiazole-4-yl]propionate (1).

Method A. To a well stirred ice-cooled (5° C.) solution of sulfur monochloride (193.3 g) in 250 mL DMF was added amino-amide .HCl (100 g, 0.47 mole) over 10 minutes. After 1 hour the reaction mixture was treated with 150 ml of ETOAc and poured into a stirring mixture of 500 g of ice and 150 mL of ETOAc. The organic layer was separated and washed with brine (2×300 mL), dried (MgSO$_4$) and concentrated to give 80 g of black tar. This was treated with 400 mL of hot cyclohexane with vigorous stirring. After cooling (22° C.), the mixture was filtered over celite. The filtrate was seeded, allowed to stand at 22° C. for 30 minutes. The crystalline mass was filtered, washed with hexane and air-dried to give 30.8 g (32.4%) of product 1: TLC, solvent system A, Rf=0.35, mp 56°-58° C. Anal. (C$_7$H$_{10}$N$_2$O$_3$S)C,H,N.

Method B. To a well stirred and ice-cooled (5° C.) solution of sulfur monochloride (2.5 mL, 0.03 mole) in 50 mL of DMF was added a solution of Isoglutamine (1.78 g, 0.01 mole) in 25 mL of DMF. The ice bath was removed and the orange-red colored solution was stirred for 16 hours. The reaction mixture was poured into ice water, the supernatant was decanted and extracted with ether (3×100 mL). The ethereal layers were combined and washed with water (2×100 mL), dried (MgSO4), and evaporated to a thick syrup. This was trituated with 200 mL of ether, filtered to eliminate sulfur granules, and concentrated to give brown solid (1.0 g), which was decolorized with activated charcoal in ethanol to give a colorless oil. This was crystallized from ethanol:cyclohexane to give a white solid: 0.8 g (46%, TLC, solvent system B, Rf=0.30, Anal. ($C_5H_6N_2$)$O_3S$), C,H,N.

The above solid was esterified with ethanol in the presence of catalytic amount of $H_2SO_4$ in an sohxlet apparatus charged with 3A molecular sieve to give: 1.0 g (86.2% of ester 1, TLC, solvent systems A, Rf=0.35.

EXAMPLE XXXIX

Ethyl 3-[3-(2,3 expoxyproxy)-1,2,5-thiadiazol-4-yl]propionate (2).

A mixture containing hydroxy-ester 2 (50.0 g, 0.25 mole), epibromohydrin (75.3 g, 0.55 mole and anhydrous potassium carbonate (76 g, 0.55 mole) in 150 mL of acetone was vigorously stirred and heated to reflux for 20 hours. The reaction mixture was filtered and washed with 100 mL of acetone. The filtrate was evaporated under reduced pressure to give an oil. This was dissolved in isopropyl ether and washed with brine, dried (MgSO4) and evaporated. The resulting oil was distilled, (bp, 43°-7° C/0.25 mm Hg) to give 30.0 g (46.4%) of product 2: TLC, solvent system A, Rf=0.58, Anal. ($C_{10}H_{14}N_2O_4S$) C,H,N.

A solution of ester-epoxide 2 (0.1 mole) and an appropriate amine (0.1 mole) in 100 mL of ethanol was heated under reflux for 3 hours and evaporated to dryness. The resulting residue was either isolated as a free base or an acid salt and crystallized or recrystallized with an appropriate solvent(s).

The above procedure was used to prepare the compounds listed in Tables V and VI.

TABLE V

R'O$_2$C—[structure with thiadiazole ring]—O—CH$_2$CH(OH)CH$_2$—NHR

| No. | R' | R | In Vitro[b] pA$_2$ Atria | Tra- chea | ug/ kg/ min. | % Inhibition of Isopropyl Induced Tachycardle | Time for 50% Recovery | Time for 80% Recovery | mp (°C.) | Free Base or Salt | Solvent(s) of Crystal- lization | Yield (%) |
|---|---|---|---|---|---|---|---|---|---|---|---|---|
| 1 | Et | CH$_2$CH$_2$NHCOCH(Me)$_2$ | 7.0 | — | 62.0 | 62 | 14[a] | 40[a] | 109–111 | Oxa- late | EtOH | 7.0 |
| 2 | Et | C(Me)$_2$CH$_2$NHCOCH(Me)$_2$ | 8.2 | — | 2.5 | 53 | 14[a] | 34[a] | 130–131 | Oxa- late | Acetone/ Ether | 30.2 |

[a]A single determination
[b]The In-vitro pA$_2$ values were obtained in guinea pig right atria, (B$_1$) and trachea (B$_2$).
[c]The beta-blocking activities were evaluated In-vivo in a canine model. The beta-blocker was infused in the animal for 3 hours with the dose adjusted to give approximately 50%. blockage of the Isoproternol-induced tachycardia. The infusion was then terminated and the time required for 80% recovery of blockade was recorded as duration of action of the compound. The amount of drug infused during the 3 hours was averaged and expressed as potency in ug/kg/min.

TABLE VI

CH$_3$CH$_2$O$_2$C—[structure with thiadiazole ring]—O—CH$_2$CH(OH)CH$_2$—NHR

| No. | R | pA$_2$ Atria | m.p. (°C.) | Free Base or Salt | Solvent of Crystallization | Yield (%) |
|---|---|---|---|---|---|---|
| 1 | C(Me)$_2$CH$_2$NHCO$_2$Et | 7.2 | 96–97 | Oxalate | EtOH/EtOAC | 14.5 |
| 2 | C(Me)$_2$CH$_2$NHCONH$_2$ | 7.4 | —[a] | Maleate | EtOH/EtOAC | 22.6 |
| 3 | CH$_2$CH$_2$NHCOCH$_3$ | 6.3 | 103–105 | Free Base | EtOH/Ether | 22.3 |
| 4 | CH(Me)CH$_2$NHCOCH$_3$ | 7.0 | 79–81 | Free Base | EtOH/Ether | 20.6 |
| 5 | C(Me)$_2$CH$_2$NHCOCH$_3$ | 7.1 | 130–131 | Oxalate | EtOAC/Ether | 23.1 |
| 6 | CH$_2$CH$_2$NHCOCH$_2$Ph | 7.1 | 99–100 | Free Base | EtOH | 33.7 |
| 7 | CH$_2$CH$_2$NHSO$_2$(N—Morpholinyl) | 6.1 | 111–113 | Oxalate- | EtOH/Ether | 16.2 |

[a]Hygroscopic solid

What is claimed is:
1. A compound of the formula

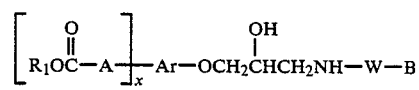

wherein R$_1$ is lower alkyl, lower cycloalkyl, lower alkenyl, lower alkynyl; A is a direct bond, lower alkylene, or lower alkenylene; x is 1 or 2, provided that when x is greater than 1, different occurrences of the

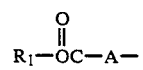

group may be the same or different; Ar is phenyl, unsubstituted or substituted with lower alkyl, lower alkenyl, lower alkynyl, lower alkoxy, halogen, acetamido, amino, nitro, lower alkylamino, hydroxy, lower hydroxyalkyl, or cyano; W is alkylene containing from 1 to about 10 carbon atoms; B is —NR$_2$SO$_2$R$_3$, —NR$_2$SO$_2$NR$_3$R$_4$, wherein R$_2$ is hydrogen or alkyl of from 1 to about 6 carbon atoms and R$_3$ and R$_4$ may be the same or different and may be hydrogen, alkyl of from 1 to about 6 carbon atoms, alkoxy wherein the alkyl group contains from 1 to about 6 carbon atoms, alkoxyalkyl wherein the alkyl groups may be the same or different and each contain from 1 to about 6 carbon atoms, cycloakyl of from 3 to about 8 carbon atoms, alkenyl of from 2 to about 6 carbon atoms, alkynyl of from 2 to about 6 carbon atoms, or a cyclopentanyl, cyclohexanyl, phenyl group, or a pharmaceutically acceptable salt thereof.

2. A compound according to claim 1 wherein R$_1$ is alkyl of from 1 to about 5 carbon atoms, and B is —NR$_2$SO$_2$R$_3$R$_4$.

3. A compound according to claim 1 wherein R$_1$ is alkyl of from 1 to about 5 carbon atoms, alkenyl of from 2 to about 5 carbon atoms, alkynyl of from 3 to about 5 carbon atoms, or cycloalkyl of from 3 to about 5 carbon atoms; or a pharmaceutically acceptable salt thereof.

4. A compound according to claim 1 wherein R$_1$ is methyl or ethyl; A is a direct bond, lower alkylene of from 1 to about 5 carbon atoms, or lower alkenylene of from 2 to about 5 carbon atoms; x is 1 or 2; W is alkylene of from 2 to about 4 carbon atoms, and R$_2$ is hydrogen; or a pharmaceutically acceptable salt thereof.

5. A compound according to claim 1 of the formula

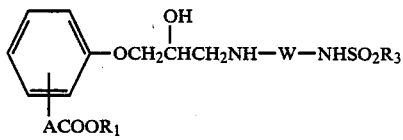

wherein R$_1$ is alkyl of from 1 to about 4 carbon atoms; A is a direct bond, alkylene of from 1 to about 3 carbon atoms, or alkenylene of from 2 to about 5 carbon atoms; W is alkylene of from 1 to about 6 carbon atoms; and R$_3$ is alkyl of from 1 to about 6 carbon atoms, alkoxy wherein the alkyl group contains from 1 to about 5 carbon atoms, phenyl which may be unsubstituted or substituted with alkyl of from 1 to about 4 carbon atoms or alkoxy of from 1 to about 4 carbon atoms, cycloalkyl of 3 to 7 carbon atoms, or a cyclopentanyl, cyclohexanyl group; or a pharmaceutically acceptable salt thereof.

6. A compound according to claim 1 of the formula

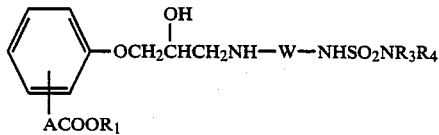

wherein R$_1$ is alkyl of from 1 to about 4 carbon atoms; A is a direct bond, alkylene of from 1 to about 3 carbon atoms, or alkenylene of from 2 to about 5 carbon atoms; W is alkylene of from 1 to about 6 carbon atoms; and R$_3$ and R$_4$ may be alike or different and represent hydrogen, alkyl of from 1 to about 4 carbon atoms, phenyl which may be unsubstituted or substituted with alkyl of from 1 to about 4 carbon atoms or alkoxy of from 1 to about 4 carbon atoms, or cycloalkyl of from 3 to about 7 carbon atoms, or a pharmaceutically acceptable salt thereof.

7. A compound according to claim 1 which is methyl 2-[2-hydroxy-3-[N-[2-[N-(4-methylphenylsulfonyl)amino]ethyl]amino]propoxy]benzoate.

8. A compound according to claim 1 which is methyl 2-[2-hydroxy-3-[N-[1,1-dimethyl-2-N'-(phenylsulfonyl)amino]ethyl]amino]propoxy]benzoate.

9. A compound according to claim 1 which is methyl 2-[2-hydroxy-3-[N-[2-[(dimethylamino)sulfonylamino]ethyl]amino]propoxy]benzoate.

10. A method for the treatment or prophylaxis of cardiac disorders in a mammal comprising administering to such mammal a shortacting β-blocking compound of the formula

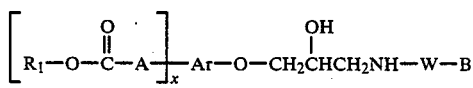

wherein R$_1$ is lower alkyl, lower cycloalkyl, lower alkenyl, lower alkynyl; A is a direct bond, lower alkylene, or lower alkenylene; x is 1 or 2, provided that when x is greater than 1, different occurrences of the

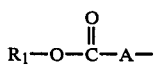

group may be the same or different; Ar is phenyl unsubstituted or substituted with lower alkyl, lower alkenyl, lower alkynyl, lower alkoxy, halogen, acetamido, amino, nitro, lower alkylamino, hydroxy, lower hydroxyalkyl or cyano; W is alkylene containing from 1 to about 10 carbon atoms; and B is —NR$_2$SO$_2$R$_3$, or —NR$_2$SO$_2$NR$_3$R$_4$, wherein R$_2$, R$_3$, and R$_4$ may each be hydrogen, alkyl, alkoxyalkyl, alkoxyaryl, cycloalkyl, alkenyl, alkynyl, except that R$_3$ and is not hydrogen when B is —NR$_2$SO$_2$R$_3$ or a pharmaceutically acceptable salt thereof.

11. The method of claim 10 wherein R$_1$ is alkyl of from 1 to about 5 carbon atoms, alkenyl of from 2 to about 5 carbon atoms, alkynyl of from 3 to about 5 carbon atoms, or cycloalkyl of from 3 to about 5 carbon atoms; or a pharmaceutically acceptable salt thereof.

12. The method of claim 10 wherein R$_1$ is methyl or ethyl; A is a direct bond, lower alkylene of from 1 to about 5 carbon atoms, or lower alkenylene of from 2 to about 5 carbon atoms, x is 1 or 2; W is alkylene of from 2 to about 4 carbon atoms, and R$_2$ is hydrogen; or a pharmaceutically acceptable salt thereof.

13. The method of claim 10 wherein the compound is of the formula

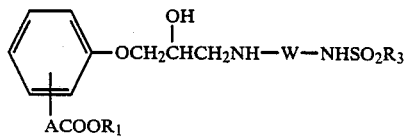

wherein R$_1$ is alkyl of from 1 to about 4 carbon atoms; A is a direct bond, alkylene of from 1 to about 3 carbon atoms, or alkenylene of from 2 to about 5 carbon atoms; W is alkylene of from 1 to about 6 carbon atoms; and R$_3$ is alkyl of from 1 to about 6 carbon atoms, alkoxy wherein the alkyl group contains from 1 to about 5 carbon atoms, phenyl which may be unsubstituted or substituted with alkyl of from 1 to about 4 carbon atoms or alkoxy of from 1 to about 4 carbon atoms, cycloalkyl of 3 to 7 carbon atoms; or a pharmaceutically acceptable salt thereof.

14. The method of claim 10 wherein the compound is of the formula

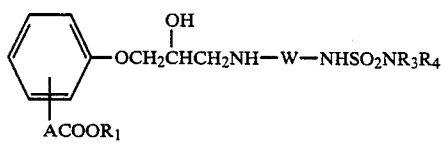

wherein $R_1$ is alkyl of from 1 to about 4 carbon atoms; A is a direct bond, alkylene of from 1 to about 3 carbon atoms, or alkenylene of from 2 to about 5 carbon atoms; W is alkylene of from 1 to about 6 carbon atoms; and $R_3$ and $R_4$ may be alike or different and represent hydrogen, alkyl of from 1 to about 4 carbon atoms, phenyl which may be unsubstituted or substituted with alkyl of from 1 to about 4 carbon atoms or alkoxy of from 1 to about 4 carbon atoms, cycloalkyl of from 3 to about 7 carbon atoms; or a pharmaceutically acceptable salt thereof.

15. A method according to claim 10 wherein the compound is administered by intravenous injection or intravenous infusion at a dosage rate of from about 0.001 to about 100 mg. of compound per kg. of body weight of said mammal per hour.

16. A method of treating glaucoma or lowering intraocular pressure in a mammal, which comprises topically applying to the eye of said mammal an intraocular pressure-lowering effective amount of a compound of the formula

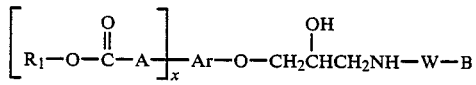

wherein $R_1$ is lower alkyl, lower cycloalkyl, lower alkenyl, lower alkynyl, A is a direct bond, lower alkylene, or lower alkenylene; x is 1 or 2, provided that when x is greater than 1, different occurrences of the

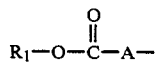

group may be the same or different; Ar is phenyl unsubstituted or substituted with lower alkyl, lower alkenyl, lower alkynyl, lower alkoxy, halogen, acetamido, amino, nitro, lower alkylamino, hydroxy, lower hydroxyalkyl or cyano; W is alkylene containing from 1 to about 10 carbon atoms; and B is $-NR_2SO_2R_3$, or $-NR_2SO_2NR_3R_4$, wherein $R_2$, $R_3$, and $R_4$ may each be hydrogen, alkyl, alkoxyalkyl, cycloalkyl, alkenyl, alkynyl, except that $R_3$ is not hydrogen when B is $-NR_2SO_2R_3$ or a pharmaceutically acceptable salt thereof.

17. The method of claim 16 wherein $R_1$ is alkyl of from 1 to about 5 carbon atoms, alkenyl of from 2 to about 5 carbon atoms, alkynyl of from 3 to about 5 carbon atoms, or cycloalkyl of from 3 to about 5 carbon atoms; or a pharmaceutically acceptable salt thereof.

18. The method of claim 16 wherein $R_1$ is methyl or ethyl; A is a direct bond, lower alkylene of from 1 to about 5 carbon atoms, or lower alkenylene of from 2 to about 5 carbon atoms; x is 1 or 2; W is alkylene of from 2 to about 4 carbon atoms, and $R_2$ is hydrogen; on a pharmaceutically acceptable salt thereof.

19. The method of claim 16 wherein the compound is of the formula

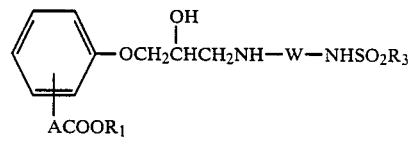

wherein $R_1$ is alkyl of from 1 to about 4 carbon atoms; A is a direct bond, alkylene of from 1 to about 3 carbon atoms, or alkenylene of from 2 to about 5 carbon atoms; W is alkylene of from 1 to about 6 carbon atoms; and $R_3$ is alkyl of from 1 to about 6 carbon atoms, alkoxy wherein the alkyl group contains from 1 to about 5 carbon atoms, phenyl which may be unsubstituted or substituted with alkyl of from 1 to about 4 carbon atoms or alkoxy of from 1 to about 4 carbon atoms, cycloalkyl of 3 to 7 carbon atoms, or a pharmaceutically acceptable salt thereof.

20. The method of claim 16 wherein the compound is of the formula

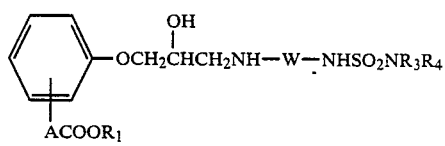

wherein $R_1$ is alkyl of from 1 to about 4 carbon atoms; A is a direct bond, alkylene of from 1 to about 3 carbon atoms, or alkenylene of from 2 to about 5 carbon atoms; W is alkylene of from 1 to about 6 carbon atoms; and $R_3$ and $R_4$ may be alike or different and represent hydrogen, alkyl of from 1 to about 4 carbon atoms, phenyl which may be unsubstituted or substituted with alkyl of from 1 to about 4 carbon atoms or alkoxy of from 1 to about 4 carbon atoms, cycloalkyl of from 3 to about 7 carbon atoms, or a pharmaceutically acceptable salt thereof.

* * * * *